US012305200B2

(12) United States Patent
Boxx

(10) Patent No.: US 12,305,200 B2
(45) Date of Patent: May 20, 2025

(54) METHODS AND COMPOSITIONS FOR VAULT NANOPARTICLE IMMOBILIZATION OF THERAPEUTIC MOLECULES AND FOR VAULT TARGETING

(71) Applicant: AUKERA, INC., Whittier, CA (US)

(72) Inventor: Gayle Boxx, Whittier, CA (US)

(73) Assignee: Aukera, Inc., Whittier, CA (US)

( * ) Notice: Subject to any disclaimer, the term of this patent is extended or adjusted under 35 U.S.C. 154(b) by 125 days.

(21) Appl. No.: 16/490,872

(22) PCT Filed: Dec. 12, 2018

(86) PCT No.: PCT/US2018/065168
§ 371 (c)(1),
(2) Date: Sep. 3, 2019

(87) PCT Pub. No.: WO2019/118572
PCT Pub. Date: Jun. 20, 2019

(65) Prior Publication Data
US 2020/0024581 A1  Jan. 23, 2020

Related U.S. Application Data

(60) Provisional application No. 62/598,378, filed on Dec. 13, 2017.

(51) Int. Cl.
*C07K 14/47* (2006.01)
*C12N 9/10* (2006.01)

(52) U.S. Cl.
CPC ............... *C12N 9/10* (2013.01); *C07K 14/47* (2013.01); *C12Y 204/0203* (2013.01); *C12N 9/1077* (2013.01)

(58) Field of Classification Search
None
See application file for complete search history.

(56) References Cited

U.S. PATENT DOCUMENTS

2016/0002305 A1  1/2016  Tanaka
2016/0367653 A1  12/2016  Rome et al.

OTHER PUBLICATIONS

Tanaka, Hideaki et al., "The structure of rat liver vault at 3.5 angsrtom resoluion." Science (2009) 323 p. 384-389.*
NCBI reference sequence NP 073206, downloaded Aug. 27, 2020.*
NCBI reference sequence NP 0010079939, downloaded Aug. 27, 2020.*
Chan, H. C. Stephen et al, "Exploring a new ligand binding site of g protein-coupled receptors." Chem. Sci. (2018) 9 p. 6480-6489.*
Peltomaa, Riikka et al, "Phage display in the quest for new selective recognition elements for biosensors." ACS Omega (2019) 4 p. 11569-11580.*
Galkov, Maksim et al, "New par1 agonist peptide demonstrates protective action in a mouse model of photothrombosis induced brain eschemia." Front. Neurosci. (2020) 14 article 335.*
Patel, Jayvaden K. et al, "Nanoscale particles-vault: a novel nanofrontier in drug delivery." Drug Develop. Deliv. (Apr. 2015.*
Smith, Jeffrey W. et al; "Protein loop grafting to construct a variant of tissue type plasminogen activator that binds platelet integrin alpha iib beta 3." J. Biol. Sci. (1995) 270 (51) p. 30486-30490.*
NCBI variation analysis of gene# 9961, run Feb. 16, 2021.*
Lobbestael, Evy et al; "Immunohistochemical detection of transgene expression in the brain using small epitope tags." BMC Biotechnol. (2010) 10(16).*
Chen, Jianqing et al; "Synthesis, stabilization and formation of [177lu]lu-amba, a systemic radiotherapeutic agent for gastrin releasing peptide receptor positive tumors." App. Radiation and Isotopes 2008) 66 p. 497-505.*
Craveur, Pierrick; et al; "Protein flexibility in the light of structural alphabets." Front. Mol. Biosci. (2015) 2(20).*
Oesterle et al, BMC Biol. (2017) 15(100).*
Gen Bank entry BC057708, available 2003.*
Berger et al., Vaults and the major vault protein: novel roles in signal pathway regulation and immunity. Cell and Molecular Life Sciences. 66(1):43-61 (2009).
Mrazek, J et al., "Polyribosomes Are Molecular 3D Nanoprinters That Orchestrate the Assembly of Vault Particles". ACS Nano. Nov. 25, 2014, Epub Oct. 30, 2014, vol. 8, No. 11; pp. 11552-11559.
PCT/US2018/065168 International Search Report and Written Opinion dated Mar. 29, 2019.
Altschul et al. Basic local alignment search tool. J Mol Biol 215(3):403-410 (1990).
Karlin et al. Methods for assessing the statistical significance of molecular sequence features by using general scoring schemes. PNAS USA 87: 2264-2268 (1990).
Karlin, et al. Applications and statistics for multiple high-scoring segments in molecular sequences. PNAS USA 90:5873-5877 (1993).
NCBI Reference Sequence NM_006437.4. *Homo sapiens* poly(ADP-ribose) polymerase family member 4 (PARP4), mRNA, Dec. 23, 2019.
NCBI Reference Sequence: NP_006428.2. Protein mono-ADP-ribosyltransferase PARP4 [*Homo sapiens*], Dec. 23, 2019.
NCBI Reference Sequence: NP_059447.2. Major vault protein isoform 1 [*Homo sapiens*], Dec. 21, 2019.

(Continued)

*Primary Examiner* — Fred H Reynolds
(74) *Attorney, Agent, or Firm* — ADRIANO & ASSOCIATES

(57) ABSTRACT

Described herein are compositions and methods for the immobilization of passenger molecules in a dense matrix of ADP-ribose within the vault particle. The present disclosure also describes a method for altering the physicomechanical properties (e.g. density, compressive strength, electrostatic properties, etc.) of packaged vaults for enhanced stability and/or downstream functionality. In addition, the present disclosure also describes compositions and methods for altering amino acid sequence of the vault protein in the vault particle by amino acid mutation, amino acid insertion and/or amino acid deletion to package passenger molecules and/or to target vault particles to specific receptors or ligands.

1 Claim, 13 Drawing Sheets

Specification includes a Sequence Listing.

(56) References Cited

OTHER PUBLICATIONS

NCBI Reference Sequence: NP_073206.2. Major vault protein [Rattus norvegicus], Dec. 25, 2019.
NCBI Reference Sequence: XP_011533233.1. Protein mono-ADP-ribosyltransferase PARP4 isoform X1 [*Homo sapiens*], Dec. 6, 2019.
NCBI Reference Sequence: XP_011533234.1. Protein mono-ADP-ribosyltransferase PARP4 isoform X2 [*Homo sapiens*], Dec. 6, 2019.
Tanaka et al. The Structure of Rat Liver Vault at 3.5 Angstrom Resolution. Science 323(5912): 384-388 (2009).
Klein SL, Strausberg RL, Wagner L, Pontius J, Clifton SW, Richardson P. Genetic and genomic tools for Xenopus research: The NIH Xenopus initiative. Dev Dyn. Dec. 2002;225(4):384-91. doi: 10.1002/dvdy.10174. PMID: 12454917.—Exhibit 1.

\* cited by examiner

| PARP | Catalytic Motif | Activity |
|------|-----------------|----------|
| 1 | H-Y-E | Y |
| 2 | H-Y-E | Y |
| 3 | H-Y-E | Y |
| 4 | H-Y-E | Y |
| 5 a/b | H-Y-E | Y |
| 6 | H-Y-I | Y |
| 7 | H-Y-I | Y |
| 8 | H-Y-I | Y |
| 9 | Q-Y-T | N |
| 10 | H-Y-I | Y |
| 11 | H-Y-I | Y |
| 12 | H-Y-I | Y |
| 13 | Y-Y-V | N |
| 14 | H-Y-L | Y |
| 15 | H-Y-L | Y |
| 16 | H-Y-Y | Y |

FIG. 3A

| ART | Catalytic Motif | Activity |
|-----|-----------------|----------|
| 1 | R-S-E | Y |
| 4 | R-S-E | Y |
| 5 | R-S-E | Y |

SEQUENCE LISTING

<160> NUMBER OF SEQ ID NOS: 20

<210> SEQ ID NO 1
<211> LENGTH: 5175
<212> TYPE: DNA
<213> ORGANISM: Homo sapiens

<400> SEQUENCE: 1

| | | | | | |
|---|---|---|---|---|---|
| atggtgatgg | gaatctttgc | aaattgtatc | ttctgtttga | aagtgaagta | cttacctcag | 60 |
| cagcagaaga | aaaagctaca | aactgacatt | aaggaaaatg | gcggaaagtt | ttcctttcg | 120 |
| ttaaatcctc | agtgcacaca | tataatctta | gataatgctg | atgttctgag | tcagtaccaa | 180 |
| ctgaattcta | tccaaaagaa | ccacgttcat | attgcaaacc | cagattttat | atggaaatct | 240 |
| atcagggaaa | agagactctt | ggatgtaaag | aattatgatc | cttataagcc | cctggacatc | 300 |
| acaccacctc | ctgatcagaa | ggcgagcagt | tctgaagtga | aaacagaagg | tctatgcccg | 360 |
| gacagtgcca | cagaggagga | agacactgtg | gaactcactg | agtttggtat | gcagaatgtt | 420 |
| gaaattcctc | atcttcctca | agattttgaa | gttgcaaaat | ataacacctt | ggagaaagtg | 480 |
| ggaatggagg | gaggccagga | agctgtggtg | gtggagcttc | agtgttcgcg | ggactccagg | 540 |

-continued

```
gactgtcctt tcctgatatc ctcacacttc ctcctggatg atggcatgga gactagaaga    600
cagtttgcta taaagaaaac ctctgaagat gcaagtgaat actttgaaaa ttacattgaa    660
gaactgaaga aacaaggatt tctactaaga gaacatttca cacctgaagc aacccaatta    720
gcatctgaac aattgcaagc attgcttttg gaggaagtca tgaattcaag cactctgagc    780
caagaggtga gcgatttagt agagatgatt tgggcagagg ccctgggcca cctggaacac    840
atgcttctca agccagtgaa caggattagc ctcaacgatg tgagcaaggc agaggggatt    900
ctccttctag taaaggcagc actgaaaaat ggagaaacag cagagcaatt gcaaaagatg    960
atgacagagt tttacagact gatacctcac aaaggcacaa tgcccaaaga agtgaacctg   1020
ggactattgg ctaagaaagc agacctctgc cagctaataa gagacatggt taatgtctgt   1080
gaaactaatt tgtccaaacc caacccacca tccctggcca aataccgagc tttgaggtgc   1140
aaaattgagc atgttgaaca gaatactgaa gaatttctca gggttagaaa agaggttttg   1200
cagaatcatc acagtaagag cccagtggat gtcttgcaga tatttagagt tggcagagtg   1260
aatgaaacca cagagttttt gagcaaaactt ggtaatgtga ggcccttgtt gcatggttct   1320
cctgtacaaa acatcgtggg aatcttgtgt cgagggttgc ttttacccaa agtagtggaa   1380
gatcgtggtg tgcaaagaac agacgtcgga aaccttggaa gtgggattta tttcagtgat   1440
tcgctcagta caagtatcaa gtactcacac ccgggagaga cagatggcac cagactcctg   1500
ctcatttgtg acgtagccct cggaaagtgt atggacttac atgagaagga ctttttccta   1560
actgaagcac caccaggcta cgacagtgtg catggagttt cgcaaacagc ctctgtcacc   1620
acagactttg aggatgatga atttgttgtc tataaaacca atcaggttaa aatgaaatat   1680
attattaaat tttccatgcc tggagatcag ataaaggact ttcatcctag tgatcatact   1740
gaattagagg aatacagacc tgagttttca aattttcaa aggttgaaga ttaccagtta   1800
ccagatgcca aaacttccag cagcaccaag gccggcctcc aggatgcctc tgggaacttg   1860
gttcctctgg aggatgtcca catcaaaggg agaatcatag acactgtagc ccaggtcatt   1920 gttttcaga catacacaaa taaaagtcac gtgcccattg aggcaaaata tatcttccct   1980
ttggatgaca aggccgctgt gtgtggcttc gaagccttca tcaatgggaa gcacatagtt   2040
ggagagatta agagaagga agaagcccag caagagtacc tagaagccgt gacccagggc   2100
catggcgctt acctgatgag tcaggatgct ccggacgttt ttactgtaag tgttggaaac   2160
ttacccccta aggctaaggt tcttataaaa attacctaca tcacagaact cagcatcctg   2220
ggcactgttg tgtctttttt catgcccgcc accgtagcac cctggcaaca ggacaaggct   2280
ttgaatgaaa accttcagga tacagtagag aagatttgta taaaagaaat aggaacaaag   2340
caaagcttct ctttgactat gtctattgag atgccgtatg tgattgaatt cattttcagt   2400
gatacacatg aactgaaaca aaagcgcaca gactgcaaag ctgtcattag caccatggaa   2460
ggcagctcct tagacagcag tggatttttct ctccacatcg gtttgtctgc tgcctatctc   2520
ccaagaatgt gggttgaaaa acatccagaa aaagaaagcg aggcttgcat gcttgtcttt   2580
caacccgatc tcgatgtcga cctccctgac ctagccagtg agagcgaagt gattatttgt   2640
cttgactgct ccagttccat ggagggtgtg acattcttgc aagccaagca aatcgccttg   2700
catgcgctgt ccttggtggg tgagaagcag aaagtaaata ttatccagtt cggcacaggt   2760
tacaaggagc tattttcgta tcctaagcat atcacaagca ataccatggc agcagagttc   2820
atcatgtctg ccacacctac catggggaac acagacttct ggaaaacact ccgatatctt   2880
agcttattgt accctgctcg agggtcacgg aacatcctcc tggtgtctga tgggcacctc   2940
```

```
caggatgaga gcctgacatt acagctcgtg aagaggagcc gcccgcacac caggttattc      3000
gcctgcggta tcggttctac agcaaatcgt cacgtcttaa ggattttgtc ccagtgtggt      3060
gccggagtat ttgaatattt taatgcaaaa tccaagcata gttggagaaa acagatagaa      3120
gaccaaatga ccaggctatg ttctccgagt tgccactctg tctccgtcaa atggcagcaa      3180
ctcaatccag atgtgcccga ggccctgcag gccccagccc aggtgccgtc cttgtttctc      3240
aatgatcgac tccttgtcta tggattcatt cctcactgca cacaggcaac tctgtgtgca      3300
ctaattcaag agaaagaatt tcgtacaatg gtgtcgacta ctgagcttca gaagacaact      3360
ggaactatga tccacaagct ggcagcccga gctctaatca gagattatga agatggcatt      3420
cttcacgaaa atgaaaccag tcatgagatg aaaaaacaaa ccttgaaatc tctgattatt      3480
aaactcagta agaaaaactc tctcataaca caatttacaa gctttgtggc agttgagaaa      3540
agggatgaga atgagtcgcc ttttcctgat attccaaaag tttctgaact tattgccaaa      3600
gaagatgtag acttcctgcc ctacatgagc tggcaggggg agcccaaaga agccgtcagg      3660
aaccagtctc ttttagcatc ctctgagtgg ccagaattac gtttatccaa acgaaaacat      3720
aggaaaattc cattttccaa aagaaaaatg gaattatctc agccagaagt ttctgaagat      3780
tttgaagagg atggcttagg tgtactacca gctttcacat caaatttgga acgtggaggt      3840
gtggaaaagc tattggattt aagttggaca gagtcatgta aaccaacagc aactgaacca      3900
ctatttaaga aagtcagtcc atgggaaaca tctacttcta gcttttttcc tattttggct      3960
ccggccgttg gttcctatct tcccccgact gcccgcgctc acagtcctgc ttccttgtct      4020
tttgcctcat atcgtcaggt agctagtttc ggttcagctg ctcctcccag acagtttgat      4080
gcatctcaat tcagccaagg ccctgtgcct ggcacttgtg ctgactggat cccacagtcg      4140
gcgtcttgtc ccacaggacc tccccagaac ccaccttctt caccctattg tggcattgtt      4200
ttttcaggga gctcattaag ctctgcacag tctgctccac tgcaacatcc tggaggcttt      4260
actaccaggc cttctgctgg caccttccct gagctggatt ctccccagct tcatttctct      4320
cttcctacag accctgatcc catcagaggt tttgggtctt atcatccctc tgcttcctct      4380
ccttttcatt ttcaaccttc cgcagcctct ttgactgcca accttaggct gccaatggcc      4440
tctgctttac ctgaggctct ttgcagtcag tcccggacta ccccagtaga tctctgtctt      4500
ctagaagaat cagtaggcag tctcgaagga agtcgatgtc ctgtctttgc ttttcaaagt      4560
tctgacacag aaagtgatga gctatcagaa gtacttcaag acagctgctt tttacaaata      4620
aaatgtgata caaaagatga cagtatcctg tgctttctgg aagtaaaaga agaggatgaa      4680
atagtgtgca tacaacactg gcaggatgct gtgccttgga cagaactcct cagtctacag      4740
acagaggatg gcttctggaa acttacacca gaactgggac ttatattaaa tcttaataca      4800
aatggtttgc acagctttct taaacaaaaa ggcattcaat ctctaggtgt aaaaggaaga      4860
gaatgtctcc tggacctaat tgccacaatg ctggtactac agtttattcg caccaggttg      4920
gaaaaagagg gaatagtgtt caaatcactg atgaaaatgg atgacgcttc tatttccagg      4980
aatattccct gggcttttga ggcaataaag caagcaagtg aatgggtaag aagaactgaa      5040
ggacagtacc catctatctg cccacggctt gaactgggga acgactggga ctctgccacc      5100
aagcagttgc tgggactcca gcccataagc actgtgtccc ctcttcatag agtcctccat      5160
tacagtcaag gctaa                                                      5175
```

<210> SEQ ID NO 2

<211> LENGTH: 1724
<212> TYPE: PRT
<213> ORGANISM: Homo sapiens

<400> SEQUENCE: 2

Met Val Met Gly Ile Phe Ala Asn Cys Ile Phe Cys Leu Lys Val Lys
1               5                   10                  15

Tyr Leu Pro Gln Gln Lys Lys Leu Gln Thr Asp Ile Lys Glu
            20                  25                  30

Asn Gly Gly Lys Phe Ser Phe Ser Leu Asn Pro Gln Cys Thr His Ile
            35                  40                  45

Ile Leu Asp Asn Ala Asp Val Leu Ser Gln Tyr Gln Leu Asn Ser Ile
50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Asp Gln Lys Ala Ser Ser Ser Glu
                100                 105                 110

Val Lys Thr Glu Gly Leu Cys Pro Asp Ser Ala Thr Glu Glu Glu Asp
            115                 120                 125

Thr Val Glu Leu Thr Glu Phe Gly Met Gln Asn Val Glu Ile Pro His
130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Glu Leu Gln Cys Ser
                165                 170                 175

Arg Asp Ser Arg Asp Cys Pro Phe Leu Ile Ser Ser His Phe Leu Leu
                180                 185                 190

Asp Asp Gly Met Glu Thr Arg Arg Gln Phe Ala Ile Lys Lys Thr Ser
            195                 200                 205

Glu Asp Ala Ser Glu Tyr Phe Glu Asn Tyr Ile Glu Glu Leu Lys Lys
210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Leu Glu Glu Val Met Asn Ser
            245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
            275                 280                 285

Ile Ser Leu Asn Asp Val Ser Lys Ala Glu Gly Ile Leu Leu Leu Val
            290                 295                 300

Lys Ala Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
                325                 330                 335

Glu Val Asn Leu Gly Leu Leu Ala Lys Lys Ala Asp Leu Cys Gln Leu
            340                 345                 350

Ile Arg Asp Met Val Asn Val Cys Glu Thr Asn Leu Ser Lys Pro Asn
            355                 360                 365

Pro Pro Ser Leu Ala Lys Tyr Arg Ala Leu Arg Cys Lys Ile Glu His
        370                 375                 380

Val Glu Gln Asn Thr Glu Glu Phe Leu Arg Val Arg Lys Glu Val Leu

```
            385                 390                 395                 400
        Gln Asn His His Ser Lys Ser Pro Val Asp Val Leu Gln Ile Phe Arg
                        405                 410                 415
        Val Gly Arg Val Asn Glu Thr Thr Glu Phe Leu Ser Lys Leu Gly Asn
                        420                 425                 430
        Val Arg Pro Leu Leu His Gly Ser Pro Val Gln Asn Ile Val Gly Ile
                        435                 440                 445
        Leu Cys Arg Gly Leu Leu Leu Pro Lys Val Val Glu Asp Arg Gly Val
                        450                 455                 460
        Gln Arg Thr Asp Val Gly Asn Leu Gly Ser Gly Ile Tyr Phe Ser Asp
        465                 470                 475                 480
        Ser Leu Ser Thr Ser Ile Lys Tyr Ser His Pro Gly Glu Thr Asp Gly
                        485                 490                 495
        Thr Arg Leu Leu Leu Ile Cys Asp Val Ala Leu Gly Lys Cys Met Asp
                        500                 505                 510
        Leu His Glu Lys Asp Phe Ser Leu Thr Glu Ala Pro Pro Gly Tyr Asp
                        515                 520                 525
        Ser Val His Gly Val Ser Gln Thr Ala Ser Val Thr Thr Asp Phe Glu
                        530                 535                 540
        Asp Asp Glu Phe Val Val Tyr Lys Thr Asn Gln Val Lys Met Lys Tyr
        545                 550                 555                 560
        Ile Ile Lys Phe Ser Met Pro Gly Asp Gln Ile Lys Asp Phe His Pro
                        565                 570                 575
        Ser Asp His Thr Glu Leu Glu Glu Tyr Arg Pro Glu Phe Ser Asn Phe
                        580                 585                 590
        Ser Lys Val Glu Asp Tyr Gln Leu Pro Asp Ala Lys Thr Ser Ser Ser
                        595                 600                 605
        Thr Lys Ala Gly Leu Gln Asp Ala Ser Gly Asn Leu Val Pro Leu Glu
                        610                 615                 620
        Asp Val His Ile Lys Gly Arg Ile Ile Asp Thr Val Ala Gln Val Ile
        625                 630                 635                 640
        Val Phe Gln Thr Tyr Thr Asn Lys Ser His Val Pro Ile Glu Ala Lys
                        645                 650                 655
        Tyr Ile Phe Pro Leu Asp Asp Lys Ala Ala Val Cys Gly Phe Glu Ala
                        660                 665                 670
        Phe Ile Asn Gly Lys His Ile Val Gly Glu Ile Lys Glu Lys Glu Glu
                        675                 680                 685
        Ala Gln Gln Glu Tyr Leu Glu Ala Val Thr Gln Gly His Gly Ala Tyr
                        690                 695                 700
        Leu Met Ser Gln Asp Ala Pro Asp Val Phe Thr Val Ser Val Gly Asn
        705                 710                 715                 720
        Leu Pro Pro Lys Ala Lys Val Leu Ile Lys Ile Thr Tyr Ile Thr Glu
                        725                 730                 735
        Leu Ser Ile Leu Gly Thr Val Gly Val Phe Phe Met Pro Ala Thr Val
                        740                 745                 750
        Ala Pro Trp Gln Gln Asp Lys Ala Leu Asn Glu Asn Leu Gln Asp Thr
                        755                 760                 765
        Val Glu Lys Ile Cys Ile Lys Glu Ile Gly Thr Lys Gln Ser Phe Ser
                        770                 775                 780
        Leu Thr Met Ser Ile Glu Met Pro Tyr Val Ile Glu Phe Ile Phe Ser
        785                 790                 795                 800
        Asp Thr His Glu Leu Lys Gln Lys Arg Thr Asp Cys Lys Ala Val Ile
                        805                 810                 815
```

Ser Thr Met Glu Gly Ser Ser Leu Asp Ser Ser Gly Phe Ser Leu His
              820                 825                 830

Ile Gly Leu Ser Ala Ala Tyr Leu Pro Arg Met Trp Val Glu Lys His
              835                 840                 845

Pro Glu Lys Glu Ser Glu Ala Cys Met Leu Val Phe Gln Pro Asp Leu
              850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
                  885                 890                 895

Gln Ile Ala Leu His Ala Leu Ser Leu Val Gly Glu Lys Gln Lys Val
              900                 905                 910

Asn Ile Ile Gln Phe Gly Thr Gly Tyr Lys Glu Leu Phe Ser Tyr Pro
              915                 920                 925

Lys His Ile Thr Ser Asn Thr Met Ala Ala Glu Phe Ile Met Ser Ala
              930                 935                 940

Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
                  965                 970                 975

Asp Gly His Leu Gln Asp Glu Ser Leu Thr Leu Gln Leu Val Lys Arg
                  980                 985                 990

Ser Arg Pro His Thr Arg Leu Phe Ala Cys Gly Ile Gly Ser Thr Ala
              995                 1000                1005

Asn Arg His Val Leu Arg Ile Leu Ser Gln Cys Gly Ala Gly Val
              1010                1015                1020

Phe Glu Tyr Phe Asn Ala Lys Ser Lys His Ser Trp Arg Lys Gln
              1025                1030                1035

Ile Glu Asp Gln Met Thr Arg Leu Cys Ser Pro Ser Cys His Ser
              1040                1045                1050

Val Ser Val Lys Trp Gln Gln Leu Asn Pro Asp Val Pro Glu Ala
              1055                1060                1065

Leu Gln Ala Pro Ala Gln Val Pro Ser Leu Phe Leu Asn Asp Arg
              1070                1075                1080

Leu Leu Val Tyr Gly Phe Ile Pro His Cys Thr Gln Ala Thr Leu
              1085                1090                1095

Cys Ala Leu Ile Gln Glu Lys Glu Phe Arg Thr Met Val Ser Thr
              1100                1105                1110

Thr Glu Leu Gln Lys Thr Thr Gly Thr Met Ile His Lys Leu Ala
              1115                1120                1125

Ala Arg Ala Leu Ile Arg Asp Tyr Glu Asp Gly Ile Leu His Glu
              1130                1135                1140

Asn Glu Thr Ser His Glu Met Lys Lys Gln Thr Leu Lys Ser Leu
              1145                1150                1155

Ile Ile Lys Leu Ser Lys Glu Asn Ser Leu Ile Thr Gln Phe Thr
              1160                1165                1170

Ser Phe Val Ala Val Glu Lys Arg Asp Glu Asn Glu Ser Pro Phe
              1175                1180                1185

Pro Asp Ile Pro Lys Val Ser Glu Leu Ile Ala Lys Glu Asp Val
              1190                1195                1200

Asp Phe Leu Pro Tyr Met Ser Trp Gln Gly Glu Pro Gln Glu Ala
              1205                1210                1215

-continued

Val Arg Asn Gln Ser Leu Leu Ala Ser Ser Glu Trp Pro Glu Leu
1220             1225                 1230

Arg Leu Ser Lys Arg Lys His Arg Lys Ile Pro Phe Ser Lys Arg
1235             1240                 1245

Lys Met Glu Leu Ser Gln Pro Glu Val Ser Glu Asp Phe Glu Glu
1250             1255                 1260

Asp Gly Leu Gly Val Leu Pro Ala Phe Thr Ser Asn Leu Glu Arg
1265             1270                 1275

Gly Gly Val Glu Lys Leu Leu Asp Leu Ser Trp Thr Glu Ser Cys
1280             1285                 1290

Lys Pro Thr Ala Thr Glu Pro Leu Phe Lys Lys Val Ser Pro Trp
1295             1300                 1305

Glu Thr Ser Thr Ser Ser Phe Phe Pro Ile Leu Ala Pro Ala Val
1310             1315                 1320

Gly Ser Tyr Leu Pro Pro Thr Ala Arg Ala His Ser Pro Ala Ser
1325             1330                 1335

Leu Ser Phe Ala Ser Tyr Arg Gln Val Ala Ser Phe Gly Ser Ala
1340             1345                 1350

Ala Pro Pro Arg Gln Phe Asp Ala Ser Gln Phe Ser Gln Gly Pro
1355             1360                 1365

Val Pro Gly Thr Cys Ala Asp Trp Ile Pro Gln Ser Ala Ser Cys
1370             1375                 1380

Pro Thr Gly Pro Pro Gln Asn Pro Pro Ser Ser Pro Tyr Cys Gly
1385             1390                 1395

Ile Val Phe Ser Gly Ser Ser Leu Ser Ser Ala Gln Ser Ala Pro
1400             1405                 1410

Leu Gln His Pro Gly Gly Phe Thr Thr Arg Pro Ser Ala Gly Thr
1415             1420                 1425

Phe Pro Glu Leu Asp Ser Pro Gln Leu His Phe Ser Leu Pro Thr
1430             1435                 1440

Asp Pro Asp Pro Ile Arg Gly Phe Gly Ser Tyr His Pro Ser Ala
1445             1450                 1455

Ser Ser Pro Phe His Phe Gln Pro Ser Ala Ala Ser Leu Thr Ala
1460             1465                 1470

Asn Leu Arg Leu Pro Met Ala Ser Ala Leu Pro Glu Ala Leu Cys
1475             1480                 1485

Ser Gln Ser Arg Thr Thr Pro Val Asp Leu Cys Leu Leu Glu Glu
1490             1495                 1500

Ser Val Gly Ser Leu Glu Gly Ser Arg Cys Pro Val Phe Ala Phe
1505             1510                 1515

Gln Ser Ser Asp Thr Glu Ser Asp Glu Leu Ser Glu Val Leu Gln
1520             1525                 1530

Asp Ser Cys Phe Leu Gln Ile Lys Cys Asp Thr Lys Asp Asp Ser
1535             1540                 1545

Ile Leu Cys Phe Leu Glu Val Lys Glu Glu Asp Glu Ile Val Cys
1550             1555                 1560

Ile Gln His Trp Gln Asp Ala Val Pro Trp Thr Glu Leu Leu Ser
1565             1570                 1575

Leu Gln Thr Glu Asp Gly Phe Trp Lys Leu Thr Pro Glu Leu Gly
1580             1585                 1590

Leu Ile Leu Asn Leu Asn Thr Asn Gly Leu His Ser Phe Leu Lys
1595             1600                 1605

Gln Lys Gly Ile Gln Ser Leu Gly Val Lys Gly Arg Glu Cys Leu

-continued

```
            1610                1615                1620

Leu Asp Leu Ile Ala Thr Met Leu Val Leu Gln Phe Ile Arg Thr
        1625                1630                1635

Arg Leu Glu Lys Glu Gly Ile Val Phe Lys Ser Leu Met Lys Met
    1640                1645                1650

Asp Asp Ala Ser Ile Ser Arg Asn Ile Pro Trp Ala Phe Glu Ala
1655                1660                1665

Ile Lys Gln Ala Ser Glu Trp Val Arg Arg Thr Glu Gly Gln Tyr
    1670                1675                1680

Pro Ser Ile Cys Pro Arg Leu Glu Leu Gly Asn Asp Trp Asp Ser
        1685                1690                1695

Ala Thr Lys Gln Leu Leu Gly Leu Gln Pro Ile Ser Thr Val Ser
    1700                1705                1710

Pro Leu His Arg Val Leu His Tyr Ser Gln Gly
        1715                1720
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Trp Ala Val Gly His Leu Met
1               5

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctgaagacac aggtagcgag tgggcggtgg ggcacttaat ggctcctgat ggcacac       57

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgtgccatc aggagccatt aagtgcccca ccgcccactc gctacctgtg tcttcag       57

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Tyr Lys Asp Asp Asp Asp Lys
1               5

<210> SEQ ID NO 7

<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctgaagacac aggtagcgat tacaaagatg acgatgataa ggctcctgat ggcacac         57

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtgtgccatc aggagcctta tcatcgtcat ctttgtaatc gctacctgtg tcttcag         57

<210> SEQ ID NO 9
<211> LENGTH: 861
<212> TYPE: PRT
<213> ORGANISM: Rattus norvegicus

<400> SEQUENCE: 9

Met Ala Thr Glu Glu Ala Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Val
        35                  40                  45

Arg Met Val Thr Val Pro Pro Arg His Tyr Cys Ile Val Ala Asn Pro
    50                  55                  60

Val Ser Arg Asp Thr Gln Ser Ser Val Leu Phe Asp Ile Thr Gly Gln
65                  70                  75                  80

Val Arg Leu Arg His Ala Asp Gln Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asn Gly Asp Lys Val Met Ala Gly Asp Glu Trp Leu
    130                 135                 140

Phe Glu Gly Pro Gly Thr Tyr Ile Pro Gln Lys Glu Val Glu Val Val
145                 150                 155                 160

Glu Ile Ile Gln Ala Thr Val Ile Lys Gln Asn Gln Ala Leu Arg Leu
                165                 170                 175

Arg Ala Arg Lys Glu Cys Phe Asp Arg Glu Lys Gly Arg Val Thr
            180                 185                 190

Gly Glu Glu Trp Leu Val Arg Ser Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Leu Gln Asn Phe Arg Asp Leu Arg Gly
225                 230                 235                 240

Val Leu His Arg Thr Gly Glu Glu Trp Leu Val Thr Val Gln Asp Thr
                245                 250                 255

```
Glu Ala His Val Pro Asp Val Tyr Glu Glu Val Leu Gly Val Pro
            260                 265                 270
Ile Thr Thr Leu Gly Pro Arg His Tyr Cys Val Ile Leu Asp Pro Met
                275                 280                 285
Gly Pro Asp Gly Lys Asn Gln Leu Gly Gln Lys Arg Val Val Lys Gly
        290                 295                 300
Glu Lys Ser Phe Phe Leu Gln Pro Gly Glu Arg Leu Glu Arg Gly Ile
305                 310                 315                 320
Gln Asp Val Tyr Val Leu Ser Glu Gln Gly Leu Leu Lys Ala
                325                 330                 335
Leu Gln Pro Leu Glu Glu Gly Ser Glu Glu Lys Val Ser His Gln
            340                 345                 350
Ala Gly Asp Cys Trp Leu Ile Arg Gly Pro Leu Glu Tyr Val Pro Ser
        355                 360                 365
Ala Lys Val Glu Val Glu Glu Arg Gln Ala Ile Pro Leu Asp Gln
    370                 375                 380
Asn Glu Gly Ile Tyr Val Gln Asp Val Lys Thr Gly Lys Val Arg Ala
385                 390                 395                 400
Val Ile Gly Ser Thr Tyr Met Leu Thr Gln Asp Glu Val Leu Trp Glu
                405                 410                 415
Lys Glu Leu Pro Ser Gly Val Glu Leu Leu Asn Leu Gly His Asp
            420                 425                 430
Pro Leu Ala Asp Arg Gly Gln Lys Gly Thr Ala Lys Pro Leu Gln Pro
        435                 440                 445
Ser Ala Pro Arg Asn Lys Thr Arg Val Val Ser Tyr Arg Val Pro His
    450                 455                 460
Asn Ala Ala Val Gln Val Tyr Asp Tyr Arg Ala Lys Arg Ala Arg Val
465                 470                 475                 480
Val Phe Gly Pro Glu Leu Val Thr Leu Asp Pro Glu Glu Gln Phe Thr
                485                 490                 495
Val Leu Ser Leu Ser Ala Gly Arg Pro Lys Arg Pro His Ala Arg Arg
            500                 505                 510
Ala Leu Cys Leu Leu Leu Gly Pro Asp Phe Phe Thr Asp Val Ile Thr
        515                 520                 525
Ile Glu Thr Ala Asp His Ala Arg Leu Gln Leu Gln Leu Ala Tyr Asn
    530                 535                 540
Trp His Phe Glu Leu Lys Asn Arg Asn Asp Pro Ala Glu Ala Ala Lys
545                 550                 555                 560
Leu Phe Ser Val Pro Asp Phe Val Gly Asp Ala Cys Lys Ala Ile Ala
                565                 570                 575
Ser Arg Val Arg Gly Ala Val Ala Ser Val Thr Phe Asp Phe His
            580                 585                 590
Lys Asn Ser Ala Arg Ile Ile Arg Met Ala Val Phe Gly Phe Glu Met
        595                 600                 605
Ser Glu Asp Thr Gly Pro Asp Gly Thr Leu Leu Pro Lys Ala Arg Asp
    610                 615                 620
Gln Ala Val Phe Pro Gln Asn Gly Leu Val Val Ser Ser Val Asp Val
625                 630                 635                 640
Gln Ser Val Glu Pro Val Asp Gln Arg Thr Arg Asp Ala Leu Gln Arg
                645                 650                 655
Ser Val Gln Leu Ala Ile Glu Ile Thr Thr Asn Ser Gln Glu Ala Ala
            660                 665                 670
```

-continued

```
Ala Lys His Glu Ala Gln Arg Leu Glu Gln Glu Ala Arg Gly Arg Leu
            675                 680                 685
Glu Arg Gln Lys Ile Leu Asp Gln Ser Glu Ala Glu Lys Ala Arg Lys
690                 695                 700
Glu Leu Leu Glu Leu Glu Ala Met Ser Met Ala Val Glu Ser Thr Gly
705                 710                 715                 720
Asn Ala Lys Ala Glu Ala Ser Arg Ala Glu Ala Ala Arg Ile Glu
                725                 730                 735
Gly Glu Gly Ser Val Leu Gln Ala Lys Leu Lys Ala Gln Ala Leu Ala
            740                 745                 750
Ile Glu Thr Glu Ala Glu Leu Glu Arg Val Lys Lys Val Arg Glu Met
            755                 760                 765
Glu Leu Ile Tyr Ala Arg Ala Gln Leu Glu Leu Glu Val Ser Lys Ala
            770                 775                 780
Gln Gln Leu Ala Asn Val Glu Ala Lys Lys Phe Lys Glu Met Thr Glu
785                 790                 795                 800
Ala Leu Gly Pro Gly Thr Ile Arg Asp Leu Ala Val Ala Gly Pro Glu
                805                 810                 815
Met Gln Val Lys Leu Leu Gln Ser Leu Gly Leu Lys Ser Thr Leu Ile
            820                 825                 830
Thr Asp Gly Ser Ser Pro Ile Asn Leu Phe Ser Thr Ala Phe Gly Leu
                835                 840                 845
Leu Gly Leu Gly Ser Asp Gly Gln Pro Pro Ala Gln Lys
850                 855                 860

<210> SEQ ID NO 10
<211> LENGTH: 893
<212> TYPE: PRT
<213> ORGANISM: Homo sapiens

<400> SEQUENCE: 10

Met Ala Thr Glu Glu Phe Ile Ile Arg Ile Pro Pro Tyr His Tyr Ile
1               5                   10                  15
His Val Leu Asp Gln Asn Ser Asn Val Ser Arg Val Glu Val Gly Pro
            20                  25                  30
Lys Thr Tyr Ile Arg Gln Asp Asn Glu Arg Val Leu Phe Ala Pro Met
        35                  40                  45
Arg Met Val Thr Val Pro Pro Arg His Tyr Cys Thr Val Ala Asn Pro
50                  55                  60
Val Ser Arg Asp Ala Gln Gly Leu Val Leu Phe Asp Val Thr Gly Gln
65                  70                  75                  80
Val Arg Leu Arg His Ala Asp Leu Glu Ile Arg Leu Ala Gln Asp Pro
                85                  90                  95
Phe Pro Leu Tyr Pro Gly Glu Val Leu Glu Lys Asp Ile Thr Pro Leu
            100                 105                 110
Gln Val Val Leu Pro Asn Thr Ala Leu His Leu Lys Ala Leu Leu Asp
            115                 120                 125
Phe Glu Asp Lys Asp Gly Asp Lys Val Val Ala Gly Asp Glu Trp Leu
130                 135                 140
Phe Glu Gly Pro Gly Thr Tyr Ile Pro Arg Lys Glu Val Glu Val Val
145                 150                 155                 160
Glu Ile Ile Gln Ala Thr Ile Ile Arg Gln Asn Gln Ala Leu Arg Leu
                165                 170                 175
Arg Ala Arg Lys Glu Cys Trp Asp Arg Asp Gly Lys Glu Arg Val Thr
            180                 185                 190
```

```
Gly Glu Glu Trp Leu Val Thr Val Gly Ala Tyr Leu Pro Ala Val
        195                 200                 205

Phe Glu Glu Val Leu Asp Leu Val Asp Ala Val Ile Leu Thr Glu Lys
210                 215                 220

Thr Ala Leu His Leu Arg Ala Arg Arg Asn Phe Arg Asp Phe Arg Gly
225                 230                 235                 240

Val Ser Arg Arg Thr Gly Glu Glu Trp Leu Thr Val Gln Asp Thr
            245                 250                 255

Glu Ala His Val Pro Asp Val His Glu Glu Val Leu Gly Val Val Pro
                260                 265                 270

Ile Thr Thr Leu Gly Pro His Asn Tyr Cys Val Ile Leu Asp Pro Val
            275                 280                 285

Gly Pro Asp Gly Lys Asn Gln Leu Gly Gln Lys Arg Val Val Lys Gly
        290                 295                 300

Glu Lys Ser Phe Phe Leu Gln Pro Gly Glu Gln Leu Glu Gln Gly Ile
305                 310                 315                 320

Gln Asp Val Tyr Val Leu Ser Glu Gln Gln Gly Leu Leu Leu Arg Ala
                325                 330                 335

Leu Gln Pro Leu Glu Glu Gly Glu Asp Glu Glu Lys Val Ser His Gln
            340                 345                 350

Ala Gly Asp His Trp Leu Ile Arg Gly Pro Leu Glu Tyr Val Pro Ser
        355                 360                 365

Ala Lys Val Glu Val Val Glu Glu Arg Gln Ala Ile Pro Leu Asp Glu
370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Pro Gly Val Glu Glu Leu Leu Asn Lys Gly Gln Asp
            420                 425                 430

Pro Leu Ala Asp Arg Gly Glu Lys Asp Thr Ala Lys Ser Leu Gln Pro
        435                 440                 445

Leu Ala Pro Arg Asn Lys Thr Arg Val Val Ser Tyr Arg Val Pro His
    450                 455                 460

Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Thr Ala Val Phe Gly Phe Glu Thr
        595                 600                 605
```

-continued

```
Ser Glu Ala Lys Gly Pro Asp Gly Met Ala Leu Pro Arg Pro Arg Asp
    610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
            645                 650                 655

Ser Val Gln Leu Ala Ile Glu Ile Thr Thr Asn Ser Gln Glu Ala Ala
        660                 665                 670

Ala Lys His Glu Ala Gln Arg Leu Glu Gln Ala Arg Gly Arg Leu
    675                 680                 685

Glu Arg Gln Lys Ile Leu Asp Gln Ser Glu Ala Glu Lys Ala Arg Lys
690                 695                 700

Glu Leu Leu Glu Leu Glu Ala Leu Ser Met Ala Val Glu Ser Thr Gly
705                 710                 715                 720

Thr Ala Lys Ala Glu Ala Ser Arg Ala Glu Ala Ala Arg Ile Glu
            725                 730                 735

Gly Glu Gly Ser Val Leu Gln Ala Lys Leu Lys Ala Gln Ala Leu Ala
        740                 745                 750

Ile Glu Thr Glu Ala Glu Leu Gln Arg Val Gln Lys Val Arg Glu Leu
    755                 760                 765

Glu Leu Val Tyr Ala Arg Ala Gln Leu Glu Leu Glu Val Ser Lys Ala
770                 775                 780

Gln Gln Leu Ala Glu Val Glu Val Lys Lys Phe Lys Gln Met Thr Glu
785                 790                 795                 800

Ala Ile Gly Pro Ser Thr Ile Arg Asp Leu Ala Val Ala Gly Pro Glu
            805                 810                 815

Met Gln Val Lys Leu Leu Gln Ser Leu Gly Leu Lys Ser Thr Leu Ile
        820                 825                 830

Thr Asp Gly Ser Thr Pro Ile Asn Leu Phe Asn Thr Ala Phe Gly Leu
    835                 840                 845

Leu Gly Met Gly Pro Glu Gly Gln Pro Leu Gly Arg Arg Val Ala Ser
850                 855                 860

Gly Pro Ser Pro Gly Glu Gly Ile Ser Pro Gln Ser Ala Gln Ala Pro
865                 870                 875                 880

Gln Ala Pro Gly Asp Asn His Val Val Pro Val Leu Arg
            885                 890

<210> SEQ ID NO 11
<211> LENGTH: 45
<212> TYPE: DNA
<213> ORGANISM: Rattus norvegicus
<220> FEATURE:
<221> NAME/KEY: CDS
<222> LOCATION: (1)..(45)

<400> SEQUENCE: 11 gag atg tct gaa gac aca ggt cct gat ggc aca ctc ctg ccc aag      45
Glu Met Ser Glu Asp Thr Gly Pro Asp Gly Thr Leu Leu Pro Lys
1               5                  10                  15

<210> SEQ ID NO 12
<211> LENGTH: 15
<212> TYPE: PRT
<213> ORGANISM: Rattus norvegicus

<400> SEQUENCE: 12

Glu Met Ser Glu Asp Thr Gly Pro Asp Gly Thr Leu Leu Pro Lys
1               5                  10                  15
```

```
<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 13 gag atg tct gaa gac aca ggt agc gct cct gat ggc aca ctc ctg ccc      48
Glu Met Ser Glu Asp Thr Gly Ser Ala Pro Asp Gly Thr Leu Leu Pro
1               5                   10                  15 aag                                                                  51
Lys

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Glu Met Ser Glu Asp Thr Gly Ser Ala Pro Asp Gly Thr Leu Leu Pro
1               5                   10                  15

Lys

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)

<400> SEQUENCE: 15 gag agc gct aag                                                      12
Glu Ser Ala Lys
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct

<400> SEQUENCE: 16

Glu Ser Ala Lys
1

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(24)
```

```
<400> SEQUENCE: 17 gag atg tct gaa gac aca ggt agc                                24
Glu Met Ser Glu Asp Thr Gly Ser
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Glu Met Ser Glu Asp Thr Gly Ser
1               5

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(27)

<400> SEQUENCE: 19 gct cct gat ggc aca ctc ctg ccc aag                            27
Ala Pro Asp Gly Thr Leu Leu Pro Lys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Ala Pro Asp Gly Thr Leu Leu Pro Lys
1               5
```

METHODS AND COMPOSITIONS FOR VAULT NANOPARTICLE IMMOBILIZATION OF THERAPEUTIC MOLECULES AND FOR VAULT TARGETING

CROSS-REFERENCE

This application claims the benefit of U.S. Provisional Application Ser. No. 62/598,378 filed Dec. 13, 2017, the entirety of which is hereby incorporated by reference herein.

FIELD OF THE DISCLOSURE

The present disclosure relates to ribonucleoprotein structures, known as vault particles or vault barrels, and methods for altering the physicomechanical properties of vault particles. Vault particles may be useful for packaging and delivering passenger molecules, (e.g., therapeutics), to target cells (e.g., cancer cells) in a subject.

Vault nanoparticles are ribonucleoprotein particles that are found in the cytoplasm of most eukaryotic cells. Vaults, by nature, are generally synthesized from 78 copies of the major vault protein (MVP) which are 3D nanoprinted by the polyribosome. These 78 copies of the MVP form the shell of the vault particle. Vaults are generally comprised of or associated with a poly-adenosine diphosphate (ADP)-ribose polymerase 4 (PARP4), also known as vault PARP (VPARP); a telomerase-associated protein 1 (TEP1); and four non-coding vault ribonucleic acids (vtRNAs).

The crystal structure of the rat vault was resolved to 3.5 Å by Tanaka et al., 2009 (Science, 2009, 323 (5912): 384-8). Each MVP monomer begins at its N-terminus with 9 structural repeat domains followed by a shoulder domain, a cap-helix domain and ends with a C-terminal cap-ring domain. Three regions within the MVP monomer could not be solved: 1) Leu429-Pro448 of repeat domain 8, 2) Met608-Pro620 of the shoulder domain (FIG. 11A), and 3) Phe846-Lys861 of the cap-ring domain). Rat MVP and human MVP share 87.8% amino acid sequence identity overall and, importantly, 91.1% identity between residues 1-861 (FIG. 9). Thus, rat and human MVP likely share similar structural features as the greatest difference is due to the extra length of the human C-terminal cap sequence.

Current methods for packaging passenger molecules into recombinant vaults are by the addition of an amino acid sequence for a passenger molecule or for a substance-binding domain to the N-terminus or to the C-terminus of the sequence of MVP (FIG. 1A, FIG. 1B). The drawback of these methods is that assembly of the vault particle may be disrupted by the addition to either the N-terminus or the C-terminus. In addition, this method restricts passenger molecules to either the waist of the vault (N-terminal fusion) or to the cap of the vault (C-terminal fusion) which may reduce packaging efficiency. Fusing a receptor or ligand peptide to the C-terminus of the cap-ring domain concentrates the molecule at the cap and may sterically hinder interaction of the monomers with their respective binding partner. Based on the crystal structure of the rat MVP, the C-terminus of the cap-ring domain is unstructured, thus it is uncertain whether a fused peptide would be exposed, partially or completely, to the outer environment. Furthermore, covalent linking of the passenger molecule to the vault complex may restrict the accessibility of that molecule and may limit its function in downstream processes. Not all molecules are able to be linked to the vault complex. Though passive packaging of passenger molecules solves the drawbacks described above, it does not allow for the packaging of smaller molecules that are able to diffuse out of the vault complex. Moreover, current methods do not address processes by which the vault particle's physicomechanical properties are altered such as stiffness (modulus), compressive strength, net charge, polarity, etc. which can affect circulation, uptake and payload delivery.

SUMMARY

The present disclosure describes immobilization of passenger molecules in a dense matrix of ADP-ribose within a vault particle. In addition, the present disclosure also describes a method for altering the physicomechanical properties (e.g. density, compressive strength, electrostatic properties, etc.) of vault particles for enhanced stability and/or downstream functionality. The present disclosure also describes a method for engineering vaults for delivery to specific cells.

In some aspects disclosed herein is a composition comprising a vault particle, a passenger molecule, and a matrix of ADP-ribose, wherein the passenger molecule and the matrix of ADP-ribose are enclosed in the vault particle. In some embodiments, the composition comprises a vault-associated protein. In some embodiments, the vault particle or a vault-associated protein is not connecting to the passenger molecule. In some embodiments, the passenger molecule is located within the vault particle, but is not connecting to the vault particle or vault-associated protein. In some embodiments, the vault particle or vault-associated protein does not possess a domain capable of connecting to the passenger molecule. In some embodiments, the vault particle or vault-associated protein does not possess a peptide capable of connecting to the passenger molecule. In some embodiments, the vault particle or vault-associated protein does not possess an amino acid capable of connecting to the passenger molecule. In some embodiments, the passenger molecule does not possess a feature capable of connecting to the vault particle or vault-associated protein. In some embodiments, connection to the vault particle or vault-associated protein comprises non-covalent interaction or binding. In some embodiments, connection to the vault particle or vault-associated protein comprises covalent interaction. In some embodiments, the passenger molecule is free within the vault particle. In some embodiments, the passenger molecule is freely encapsulated by the vault during vault assembly. In some embodiments, the passenger molecule is fused to a carboxyl terminus of the vault particle. In some embodiments, the passenger molecule is fused to an amino terminus of the vault nanoparticle. In some embodiments, the passenger molecule is fused to a mINT domain of the vault-associated protein. In some embodiments, the passenger molecule is not fused to a mINT domain of the vault-associated protein. In some embodiments, the vault-associated protein is PARP4. In some embodiments, the vault-associated protein comprises a poly-adenosine diphosphate (ADP)-ribose polymerase protein. In some embodiments, the passenger molecule has a molecular weight of less than about 900 daltons. In some embodiments, the passenger molecule has a molecular weight that is equal to or greater than about 900 daltons. In some embodiments, the passenger molecule is a chemotherapy medication. In some embodiments, the passenger molecule is doxorubicin.

In some aspects, disclosed herein is a method for producing a vault particle, comprising ADP-ribosylation of a vault enclosed passenger molecule resulting in an ADP-ribose matrix that immobilizes the vault-enclosed passenger molecule. In some embodiments, the ADP-ribosylation is catalyzed by PARP4. In some embodiments, enclosing the passenger molecule in the vault is while producing the vault particle. In some embodiments, the passenger molecule is enclosed within the vault after producing the vault particle. In some embodiments, the passenger molecule comprises an acceptor site for ADP-ribose. In some embodiments, the vault protein of the vault particle comprises an acceptor for ADP-ribose. In some embodiments, the method of synthesizing the vault particle uses an in vitro cell-free protein expression system. In some embodiments, the method of synthesizing the vault particle uses a cell-based protein expression system. In some embodiments, the ADP-ribosylation is due to a presence of a PARP4 protein. In some embodiments, NAD+ or an NAD+ analog is used as a substrate for ADP-ribosylation. In some embodiments, the method does not comprise connecting the passenger molecule to the vault particle or a vault-associated protein. In some embodiments, the method comprises encapsulating the passenger molecule within the vault particle, but not connecting the passenger molecule to the vault particle or a vault-associated protein. In some embodiments, the method comprises fusing the passenger molecule to a carboxyl terminus of the vault particle. In some embodiments, the method comprises fusing the passenger molecule to an amino terminus of the vault nanoparticle.

In some aspects, described herein is a method for ADP-ribosylation of a vault enclosed molecule that is catalyzed by a vault-associated protein and that results in an ADP-ribose matrix that traps a passenger molecule. In some embodiments the vault-associated protein is a PARP. In some embodiments, the vault-associated protein is PARP4 or an engineered variant of PARP4. In some embodiments, the physicomechanical properties of the vault particle are altered by ADP-ribosylation. In some embodiments, a cofactor is added the vault to alter the physicomechanical properties of the vault particle. In some embodiments, a lipid is added to the vault to alter the physicomechanical properties of the vault particle. In some embodiments, the passenger molecule is enclosed in the vault during the production of the vault particle. In some embodiments, the method for ADP-ribosylation of the vault enclosed molecule comprises contacting a vault protein of the vault particle with an excipient molecule that has an acceptor site for ADP-ribose. In some embodiments, the method of synthesizing the vault particle comprises an in vitro cell-free protein expression system. In some embodiments, the method of synthesizing the vault particle comprises a cell-based protein expression system. In some embodiments, the method for producing the vault particle comprises using NAD+ or an NAD+ analog as a substrate for ADP-ribosylation. In some embodiments, the passenger molecule is encapsulated within but not connected to the vault particle or a vault-associated protein. In some embodiments, the passenger molecule is fused to a carboxyl terminus of the vault particle. In some embodiments, the passenger molecule is fused to an amino terminus of the vault nanoparticle.

In some aspects, disclosed herein is method of delivering a vault particle to a cell, wherein the vault particle comprises an enclosed, immobilized passenger molecule within a matrix of ADP-ribose. In some embodiments, the vault particle localizes to the nucleus of the cell. In some embodiments, the cell is a cancer cell. In some embodiments, the cancer cell is from breast or prostate cancer.

In some aspects, disclosed herein is a method of treating a condition in a subject in need thereof, comprising administering a vault particle to the subject, wherein the vault particle comprises an enclosed, immobilized passenger molecule within a matrix of ADP-ribose.

In some aspects, disclosed herein is a method of treating a condition in a subject in need thereof, comprising administering the compositions as disclosed in this application.

In some aspects, disclosed herein is a composition comprising a vault particle, wherein the vault particle comprises multiple copies of a modified sequence of major vault protein (MVP), wherein the modified sequence comprises a mutation or insertion of specific at least one amino acid which results in a change in the local charge, hydrophobicity or polarity of the region. In some embodiments, the sequence of MVP comprises a mutation of one or more amino acids. In some embodiments, the sequence of MVP comprises an insertion of one or more amino acids. In some embodiments, the mutation or insertion is located in a shoulder domain of the MVP. In some embodiments, the mutation or insertion results in expression of a receptor or ligand binding peptide.

In some aspects, described herein is a method of producing a modified major vault protein for a vault particle, comprising: obtaining at least one nucleic acid having a sequence encoding a major vault protein: modifying a region of the sequence encoding a region of the major vault protein, wherein the region faces the interior of the vault particle; and performing at least one of transcription and translation to obtain the modified major vault protein. In some embodiments, the region comprises a loop. In some embodiments, the region comprises a side chain. In some embodiments, the region comprises a shoulder domain. In some embodiments, modifying the region comprises nucleic acid mutagenesis. In some embodiments, the nucleic acid mutagenesis comprises introducing at least one of an amino acid substitution, amino acid deletion and amino acid insertion. In some embodiments, the region for modification is identified and chosen by obtaining and reviewing a crystal structure of a major vault protein. In some embodiments, the modified major vault protein is capable of forming a non-covalent interaction with a passenger molecule that the unmodified major vault protein is not capable of forming.

In some aspects, disclosed herein is a composition comprising a vault particle, a passenger molecule, and a matrix of ADP-ribose, wherein the passenger molecule and the matrix of ADP-ribose are enclosed in the vault particle. In some embodiments, the compositions comprise a vault-associated protein wherein the vault-associated protein is a poly-adenosine diphosphate (ADP)-ribose polymerase protein. In some embodiments, the passenger molecule is located within the vault particle but is not connected to the vault particle or vault-associated protein and does not possess a feature, an amino acid, a domain or a peptide capable of connecting to the passenger molecule. In some embodiments, the passenger molecule is free within the vault particle or the passenger is freely encapsulated by the vault during vault assembly. In some embodiments, the passenger molecule is fused to a carboxyl terminus of the vault particle, the passenger molecule is fused to an amino terminus of the vault particle, or the passenger molecule is fused to a mINT domain of the vault-associated protein.

In some aspects, disclosed herein is a method for producing a vault particle, comprising ADP-ribosylation of a vault enclosed passenger molecule, resulting in an ADP-ribose matrix that immobilizes or traps the vault-enclosed passenger molecule. In some embodiments, the ADP-ribosylation is catalyzed by an engineered poly-adenosine diphosphate (ADP)-ribose polymerase protein. In some embodiments, the passenger molecule, excipient molecule or the vault protein of the vault particle comprises an acceptor site for ADP-ribose. In some embodiments, NAD+ or an NAD+ analog is used as a substrate for ADP-ribosylation. In some embodiments, the vault particle comprises altered physicomechanical properties. In some embodiments the vault particle localizes to the nucleus of the cell.

In some aspects, disclosed herein is a composition comprising a vault particle, wherein the vault particle comprises multiple copies of a modified major vault protein (MVP), wherein the modified sequence comprises a mutation or insertion of at least one amino acid which results in a change in the local charge, hydrophobicity, polarity of the region and/or affinity or avidity for a binding partner. In some embodiments, the sequence of MVP comprises a mutation, insertion or deletion of one or more amino acids. In some embodiments, the mutation, insertion or deletion results in expression of a modified major vault protein forming a non-covalent interaction with a passenger molecule that an unmodified major vault protein is not capable of forming. In some embodiments, the mutation, insertion and/or deletion results in expression of a receptor or ligand binding peptide. In some embodiments, the mutation, insertion and/or deletion is located in a shoulder domain of the MVP.

In some aspects, disclosed herein is a method of producing a modified major vault protein for a vault particle, comprising: obtaining at least one nucleic acid having a sequence encoding an unmodified major vault protein; modifying a region of the sequence encoding a region of the unmodified major vault protein, wherein the region faces the interior of the vault particle; and performing at least one of transcription and translation to obtain the modified major vault protein. In some embodiments, the region comprises a loop, a side chain or a shoulder domain. In some embodiments, nucleic acid mutagenesis comprises introducing at least one of an amino acid substitution, amino acid deletion and amino acid insertion. In some embodiments, the modified major vault protein is capable of forming a non-covalent interaction with a passenger molecule that the unmodified major vault protein is not capable of forming. In some embodiments, the vault particle comprises altered physicomechanical properties. In some embodiments the vault particle localizes to the nucleus of the cell.

In some aspects, disclosed herein is a method of treating a condition in a subject in need thereof, comprising administering a vault particle to the subject, wherein the vault particle comprises an enclosed, immobilized passenger molecule within a matrix of ADP-ribose.

In some aspects, disclosed herein is a method of treating a condition in a subject in need thereof, comprising administering the compositions as disclosed in this application.

BRIEF DESCRIPTION OF THE DRAWINGS

FIG. 1A shows the passenger molecules are fused to the caps (carboxyl-terminus) of the vault nanoparticle. FIG. 1B shows the passenger molecules are fused to the waist (amino-terminus) of the vault nanoparticle. FIG. 1C shows the passenger molecules are fused to the mINT domain of PARP4. FIG. 1D shows the passenger molecules are freely encapsulated by the vault during vault assembly.

FIG. 3A shows alignment of the ADP-ribosyltransferase catalytic motif of human PARPs and their activity state. FIG. 3B shows alignment of the catalytic motif of arginine specific ADP-ribosyltransferses (ARTs).

FIG. 5A shows encapsulation of passenger molecules during vault synthesis. FIG. 5B shows co-incubation of passenger molecules with completed vaults. FIG. 5C shows a legend describing features shown in FIGS. 5A and 5B.

FIG. 6A schematic representation of agarose gel electrophoresis and vault mobility based on charge; vaults containing PARP4 (right lane) and vaults without PARP4 (left lane) following incubation with a small molecule and NAD+ in ADP-ribosylation buffer. FIG. 6B shows migration of vaults in a native agarose gel based on charge; vaults containing PARP4 (right lane) and vaults without PARP4 (left lane) following incubation with a small molecule and NAD+ in ADP-ribosylation buffer.

Figure 9:
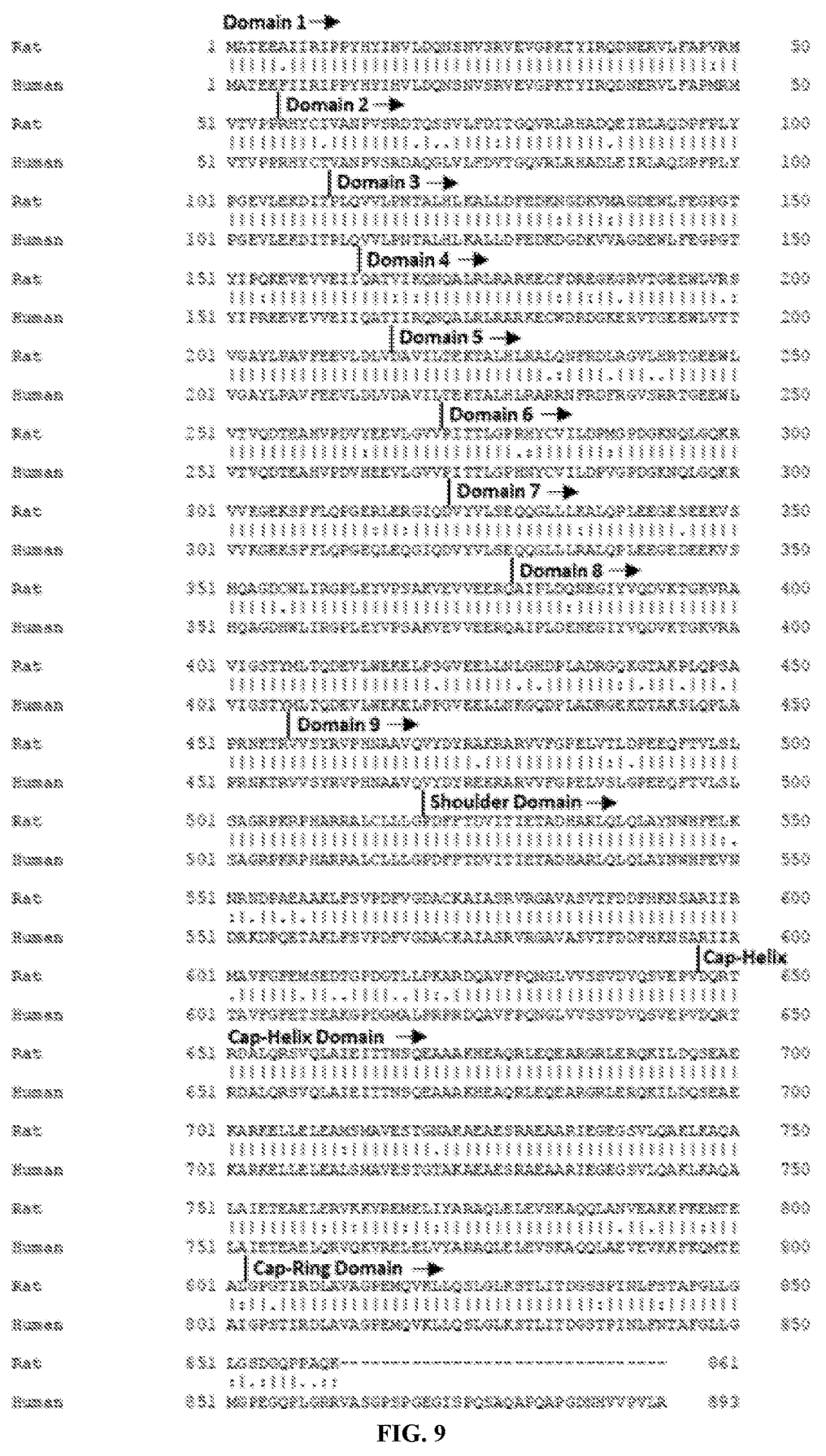

FIG. 9 shows an alignment of the amino acid sequence of rat MVP (NCBI GenBank NP_073206.2) and human MVP
(SEQ. ID NO.: 9)

MATEEAIIRIPPYHYIHVLDQNSNVSRVEVGPKTYIRQDNERVLFAPVR

MVTVPPRHYCIVANPVSRDTQSSVLFDITGQVRLRHADQEIRLAQDPFP

LYPGEVLEKDITPLQVVLPNTALHLKALLDFEDKNGDKVMAGDEWLFEG

PGTYIPQKEVEVVEIIQATVIKQNQALRLRARKECFDREGKGRVTGEEW

LVRSVGAYLPAVFEEVLDLVDAVILTEKTALHLRALQNFRDLRGVLHRT

GEEWLVTVQDTEAHVPDVYEEVLGVVPITTLGPRHYCVILDPMGPDGKN

QLGQKRVVKGEKSFFLQPGERLERGIQDVYVLSEQQGLLLKALQPLEEG

ESEEKVSHQAGDCWLIRGPLEYVPSAKVEVVEERQAIPLDQNEGIYVQD

VKTGKVRAVIGSTYMLTQDEVLWEKELPSGVEELLNLGHDPLADRGQKG

TAKPLQPSAPRNKTRVVSYRVPHNAAVQVYDYRAKRARVVFGPELVTLD

PEEQFTVLSLSAGRPKRPHARRALCLLLGPDFFTDVITIETADHARLQL

QLAYNWHFELKNRNDPAEAAKLFSVPDFVGDACKAIASRVRGAVASVTF

DDFHKNSARIIRMAVFGFEMSEDTGPDGTLLPKARDQAVFPQNGLVVSS

VDVQSVEPVDQRTRDALQRSVQLAIEITTNSQEAAAKHEAQRLEQEARG

RLERQKILDQSEAEKARKELLELEAMSMAVESTGNAKAEAESRAEAARI

EGEGSVLQAKLKAQALAIETEAELERVKKVREMELIYARAQLELEVSKA

-continued

QQLANVEAKKFKEMTEALGPGTIRDLAVAGPEMQVKLLQSLGLKSTLIT

DGSSPINLFSTAFGLLGLGSDGQPPAQK (NCBI GenBank NP_059447.2)

(SEQ. ID NO.: 10)
MATEEFIIRIPPYHYIHVLDQNSNVSRVEVGPKTYIRQDNERVLFAPMR

MVTVPPRHYCTVANPVSRDAQGLVLFDVTGQVRLRHADLEIRLAQDPFP

LYPGEVLEKDITPLQVVLPNTALHLKALLDFEDKDGKVVAGDEWLFEG

PGTYIPRKEVEVVEIIQATIIRQNQALRLRARKECWDRDGKERVTGEEW

LVTTVGAYLPAVFEEVLDLVDAVILTEKTALHLRARRNFRDFRGVSRRT

GEEWLVTVQDTEAHVPDVHEEVLGVVPITTLGPHNYCVILDPVGPDGKN

QLGQKRVVKGEKSFFLQPGEQLEQGIQDVYVLSEQQGLLLRALQPLEEG

EDEEKVSHQAGDHWLIRGPLEYVPSAKVEVVEERQAIPLDENEGIYVQD

VKTGKVRAVIGSTYMLTQDEVLWEKELPPGVEELLNKGQDPLADRGEKD

TAKSLQPLAPRNKTRVVSYRVPHNAAVQVYDYREKRARVVFGPELVSLG

PEEQFTVLSLSAGRPKRPHARRALCLLLGPDFFTDVITIETADHARLQL

QLAYNWHFEVNDRKDPQETAKLFSVPDFVGDACKAIASRVRGAVASVTF

DDFHKNSARIIRTAVFGFETSEAKGPDGMALPRPRDQAVFPQNGLVVSS

VDVQSVEPVDQRTRDALQRSVQLAIEITTNSQEAAAKHEAQRLEQEARG

RLERQKILDQSEAEKARKELLELEALSMAVESTGTAKAEAESRAEAARI

EGEGSVLQAKLKAQALAIETEAELQRVQKVRELELVYARAQLELEVSKA

QQLAEVEVKKFKQMTEAIGPSTIRDLAVAGPEMQVKLLQSLGLKSTLIT

DGSTPINLENTAFGLLGMGPEGQPLGRRVASGPSPGEGISPQSAQAPQA

PGDNHVVPVLR.

Domains are annotated based on the crystal structure of the rat vault solved by Tanaka et al 2009 (Science, 2009, 323 (5912): 384-8).

Figure 10A:
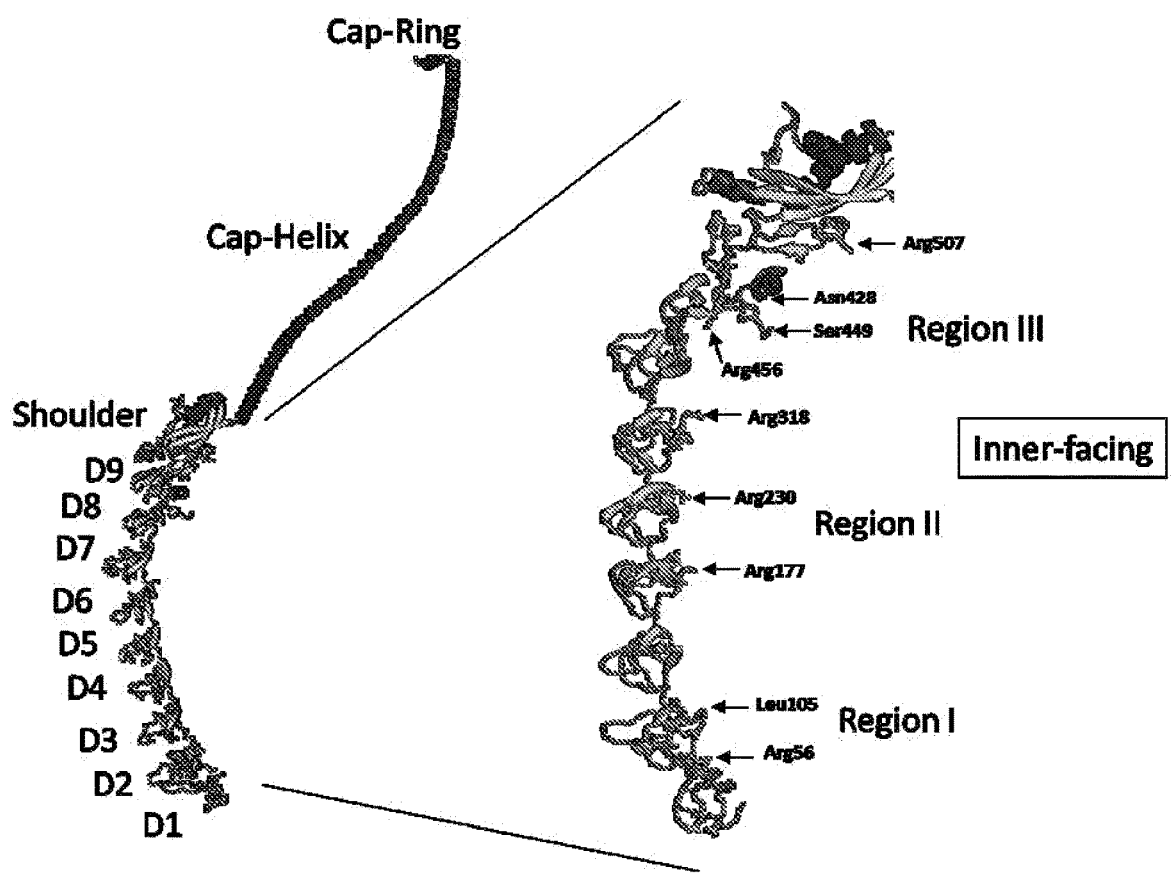
Figure 10B:
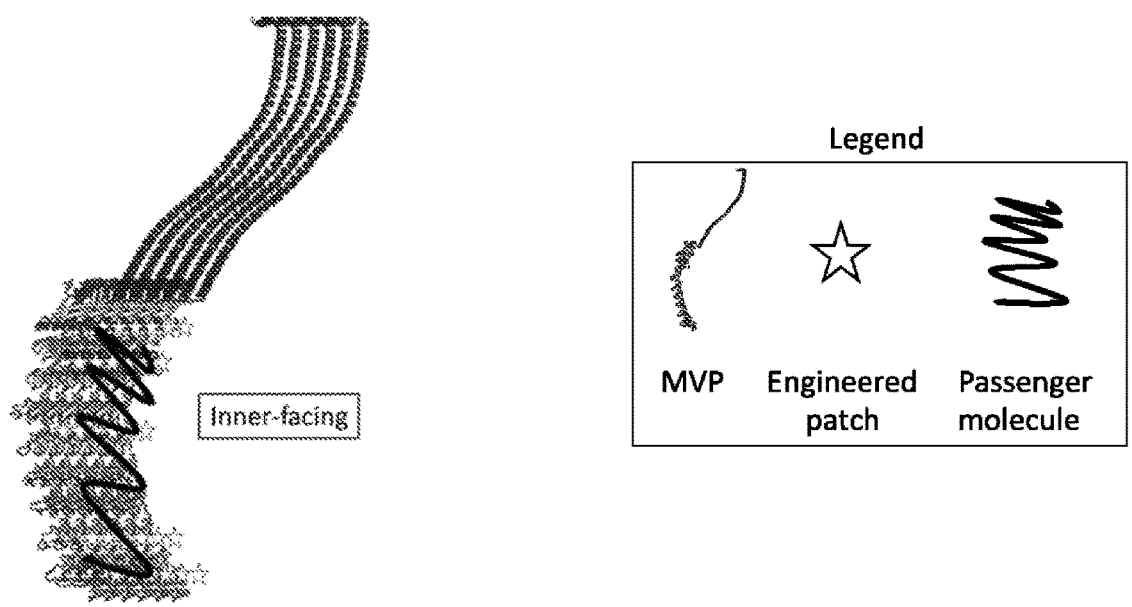

FIG. 10A-FIG. 10B show cartoon representations of the rat MVP. FIG. 10A shows the domain structure and select inner-facing loops and select amino acid side chains. FIG. 10B shows the binding of a passenger molecule through multiple, engineered non-covalent interactions spread throughout the vault barrel.

Figure 11A:
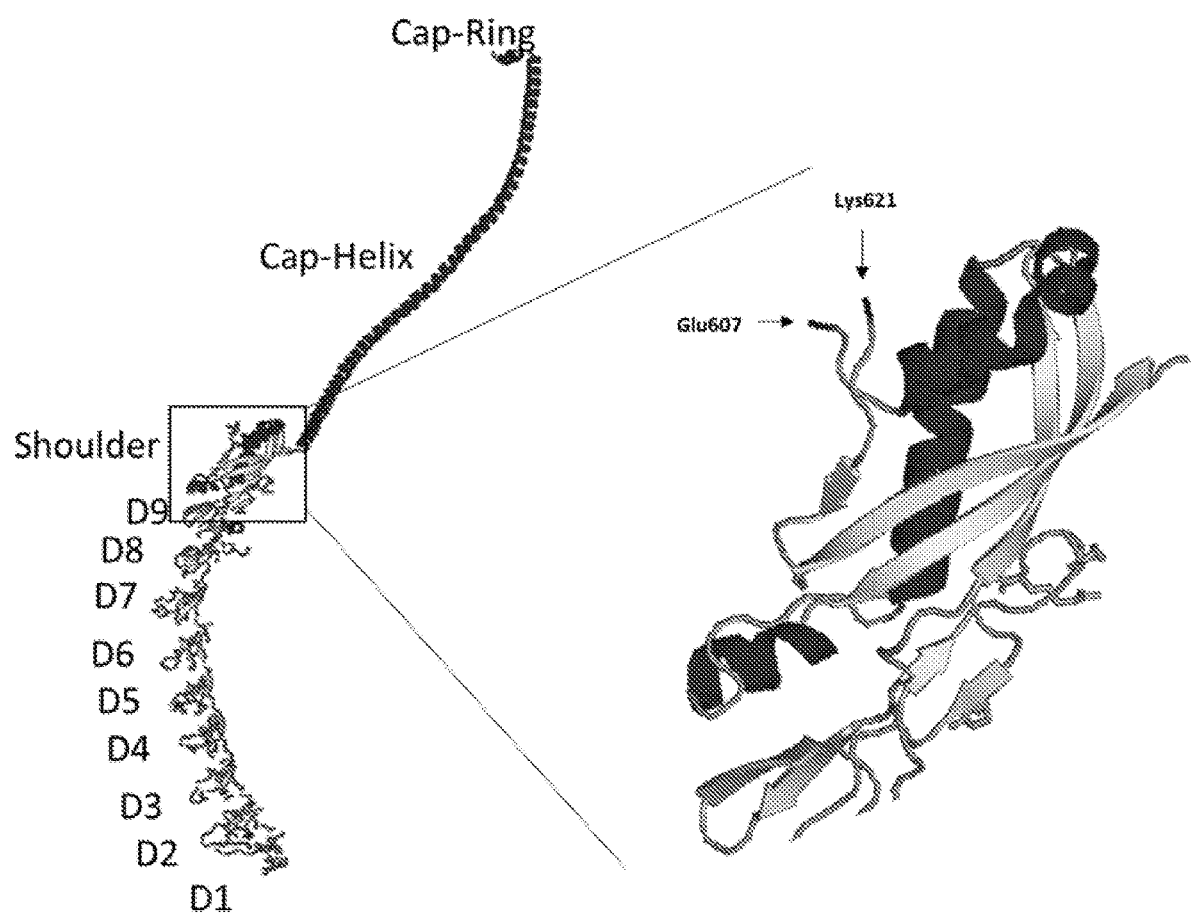
Figure 11B:
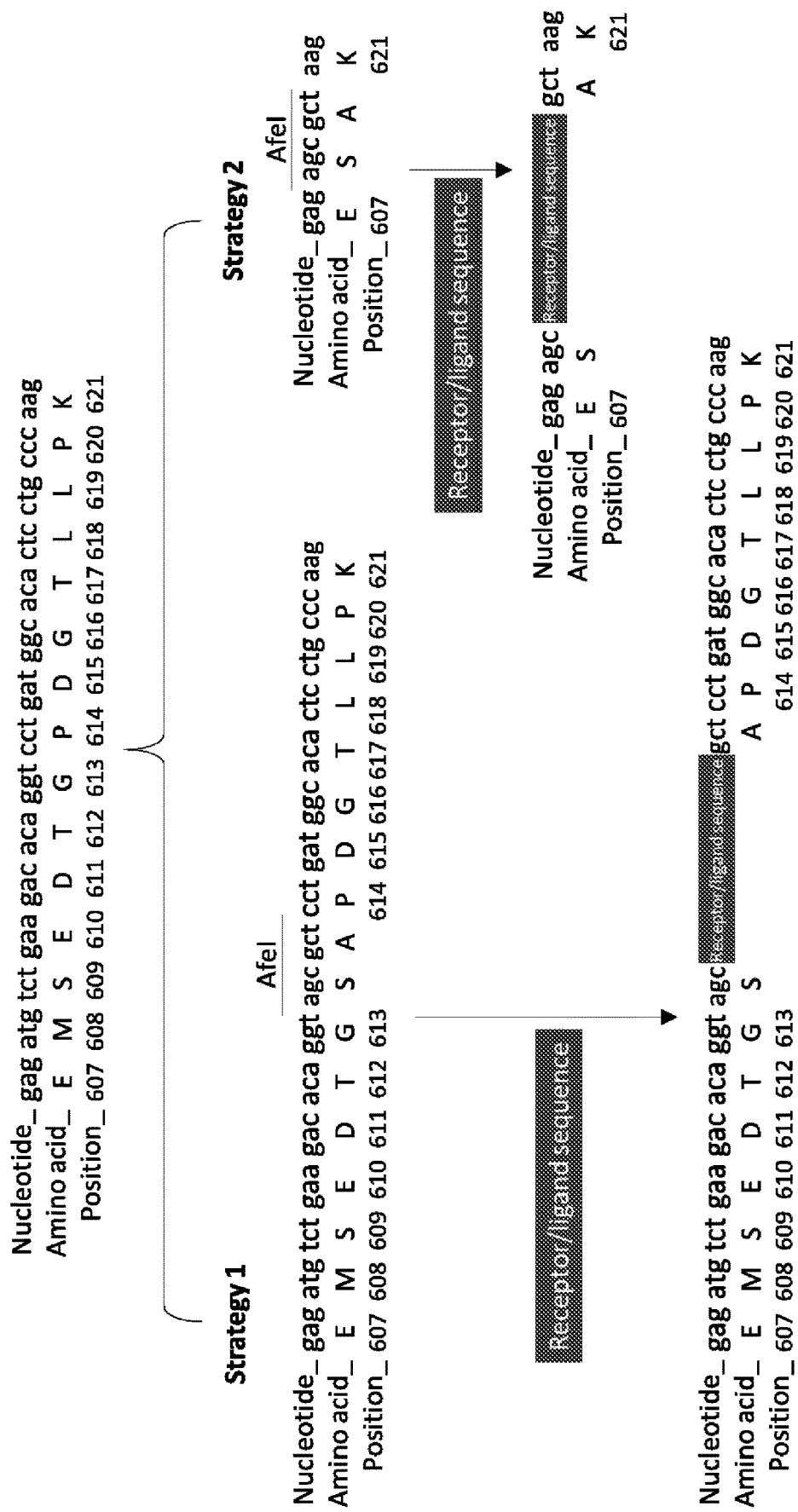

FIG. 11A-FIG. 11B shows a cartoon representation of the rat MVP and strategies to insert sequences into the shoulder domain. FIG. 11A shows the shoulder domain and the unstructured outer-facing region in the shoulder domain. FIG. 11B shows two non-limiting example strategies for introducing receptor or ligand peptides into the shoulder domain. FIG. 11B also includes sequences (SEQ ID NO.: 11)
GAGATGTCTGAAGACACAGGTCCTGATGGCACACTCCTGCCCAAG, (SEQ ID NO.: 12)
EMSEDTGPDGTLLPK, (SEQ ID NO.: 13)
GAGATGTCTGAAGACACAGGTAGCGCTCCTGATGGCACACTCCTGCCCAAG, (SEQ ID NO.: 14)
EMSEDTGSAPDGTLLPK, (SEQ ID NO.: 15)
GAGAGCGCTAAG, (SEQ ID NO.: 16)
ESAK, (SEQ ID NO.: 17)
GAGATGTCTGAAGACACAGGTAGC, (SEQ ID NO.: 18)
EMSEDTGS, (SEQ ID NO.: 19)
GCTCCTGATGGCACACTCCTCCCCAAG, and (SEQ ID NO.: 20)
APDGTLLPK.

Figure 12A:
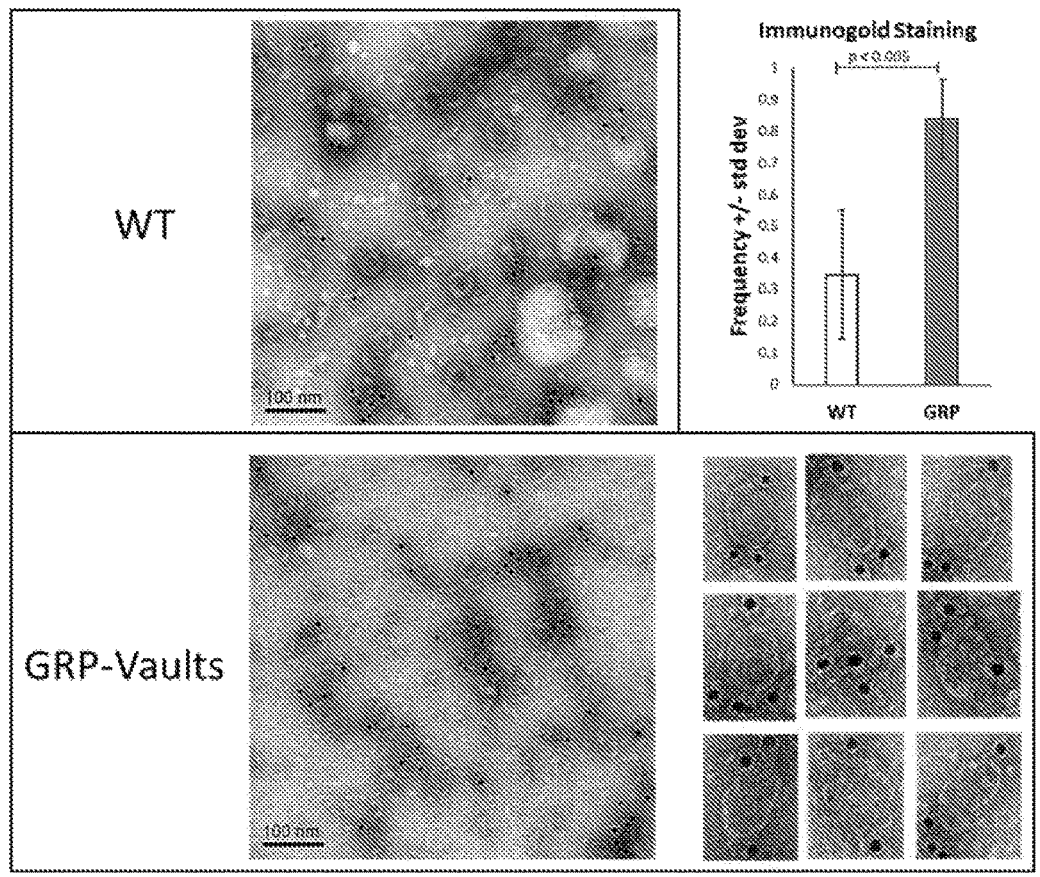
Figure 12B:
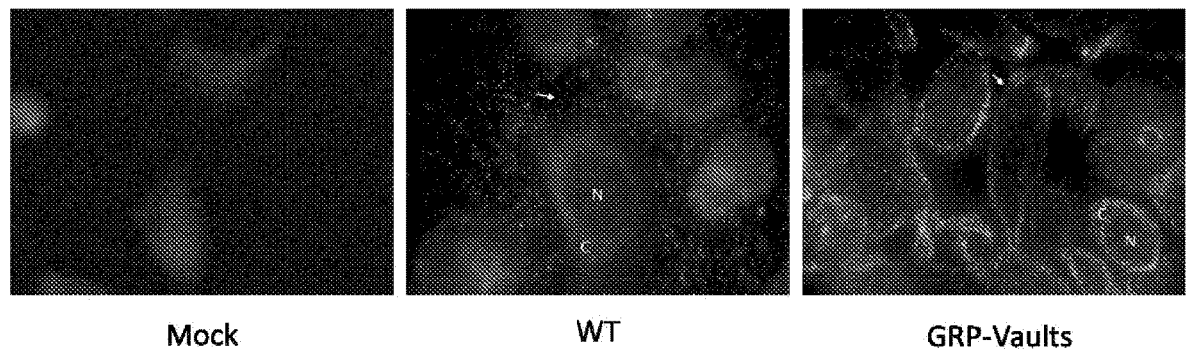

FIG. 12A-FIG. 12B shows assembly and functional activity of rat vault nanoparticles modified to express the gastrin releasing peptide (GRP) ligand in the unstructured region of the shoulder domain. FIG. 12A shows representative immunogold electron micrographs of wild type and gastrin releasing peptide receptor (GRPR) targeting vaults stained with rabbit anti-gastrin releasing peptide and goat anti-rabbit IgG-10 am gold. Frequency of immunogold labeling of vaults is plotted as the mean and standard deviation (Two-tailed T-test) and representative, individual immunogold labeled GRP-Vaults are shown below. FIG. 12B shows an in vitro binding assay with Dylight-488 labeled wild type vaults or Dylight-488 labeled GRPR targeting vaults and a human prostate cancer cell line, PC-3, that expresses GRPR. C, cytoplasm; N, nucleus; arrow, a single vault particle.

TERMINOLOGY

In the following description, certain specific details are set forth in order to provide a thorough understanding of various embodiments. However, one skilled in the art will understand that the embodiments provided may be practiced without these details.

Unless the context requires otherwise, throughout the specification and claims which follow, the word "comprise" and variations thereof, such as, "comprises" and "comprising" are to be construed in an open, inclusive sense, that is, as "including, but not limited to."

As used herein, the terms "vault", "vault particle" and "vault nanoparticle," are used interchangeably to refer to a complex of major vault proteins (MVP) that are synthesized to form a vault with an internal cavity. In some embodiments, the vault is synthesized with a 3D nanoprinting technique. In some embodiments, the vault has an ovoid shape.

As used herein, the term, "ADP-ribosylation," generally refers to the enzyme catalyzed reaction whereby one (mono) or more (poly) ADP-ribose units derived from the substrate are covalently linked to an acceptor molecule, unless otherwise noted.

As used herein, the term, "substrate," generally refers to NAD+ or analogs of NAD+, unless otherwise noted.

As used herein, the term, "passenger molecule," generally refers to one or more molecules (e.g., proteins, carbohydrates, nucleic acids, lipids, small molecules, active pharmaceutical ingredients etc. and combinations thereof) that are completely or partially enclosed within the vault particle or expressed on the outer-facing surface of the vault particle.

As used in this specification and the appended claims, the singular forms "a." "an." and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by about 10%, 5%, or 1%.

As used herein, the terms "homologous." "homology." "percent homologous," or "percent homology," when used herein to describe an amino acid sequence or a nucleic acid sequence, relative to a reference sequence, can be determined using the formula described by Karlin and Altschul (Proc. Natl. Acad. Sci. USA 87:2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215:403-410, 1990). Percent homology of sequences can be determined using the most recent version of BLAST, as of the filing date of this application.

DETAILED DESCRIPTION OF THE DISCLOSURE

Figure 1A:
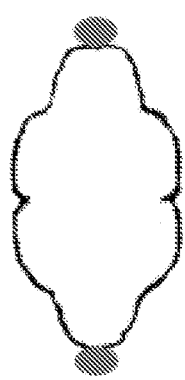
FIG. 1A-FIG. 1D show schematic diagrams of current vault packaging strategies represented as a longitudinal cross-section.
Figure 1B:
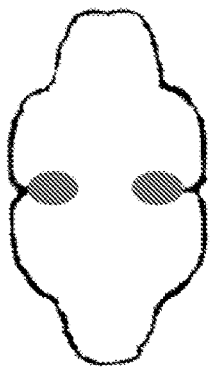
Figure 1C:
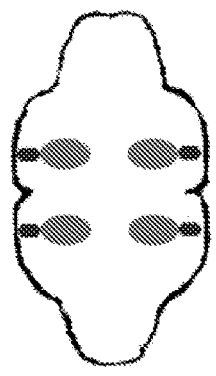
Figure 1D:
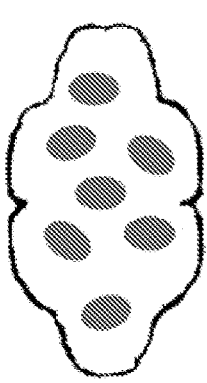

Targeted delivery of therapeutics to cells, such as abnormal or cancerous cells, is critical to minimize off-target effects including toxicity and autoimmune responses. Vault nanoparticles containing passenger molecules (e.g., therapeutics) may be used for such targeted delivery. Targeting a vault nanoparticle to a cell typically requires a receptor or ligand on the outer-facing surface of the vault particle that is accessible to bind to its respective ligand or receptor (e.g., on a target cell) (FIG. 1A). Passenger molecules of interest can be packaged into recombinant vaults by either linking them to the MVP (FIGS. 1A and B) or to the major vault interaction domain (mINT) of PARP4 (FIG. 1C), or by passive encapsulation during vault synthesis (FIG. 1D).

Figure 2:
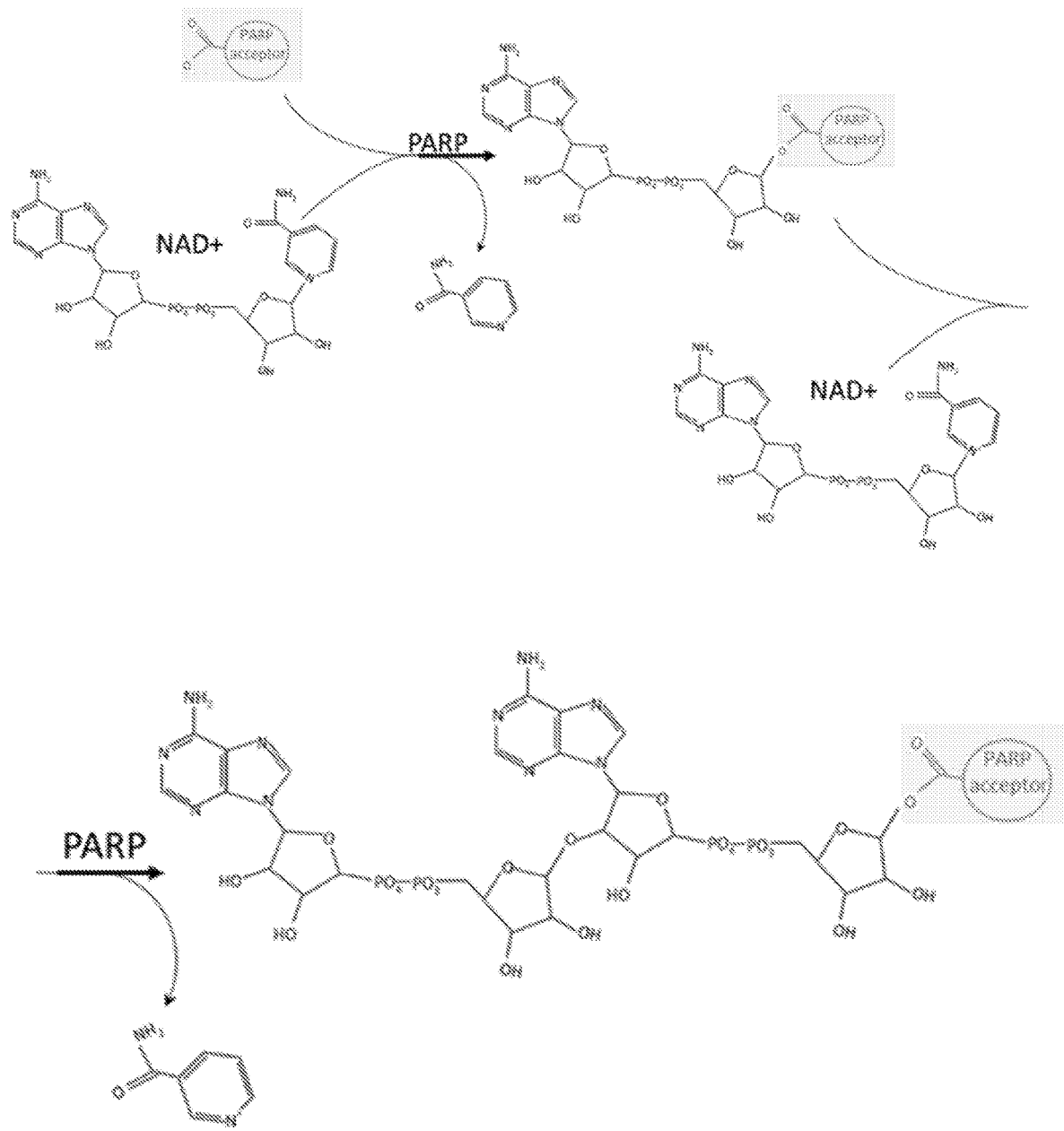
FIG. 2 shows an ADP-ribosylation reaction. An ester bond forms between the acceptor molecule and the first ADP-ribose of NAD+. Polymerization of an ADP-ribose chain occurs through 2'-1' glycosidic bond formation, in a linear fashion, and branching may occur after 20 ADP-ribose units to create a dense matrix.

The PARP family of enzymes makes up one subclass of ADP-ribosyltransferases which are capable of mediating ADP-ribosylation. ADP-ribosylation is the addition of ADP-ribose onto an acceptor molecule (see, e.g., FIG. 2). This process is catalyzed by an ADP-ribosyltransferase (e.g., PARP4), and uses NAD+ as the substrate. ADP-ribosylation requires acceptor sites on these acceptor molecules, such as a carboxyl group on aspartic acid, glutamic acid, and an amine group on lysine. MVP, PARP4, NAD+ and NAD+ analogs may serve as acceptors for ADP-ribosylation to some degree. Thus, to achieve ADP-ribosylation inside the vault, acceptor sites may be present on target passenger molecules, passenger excipients, and/or a vault protein (MVP, PARP, TEP).

PARPs are predominately defined by a H-Y-E catalytic motif (see, e.g., FIG. 3A), while the other subclass of ADP-ribosyltransferases have a R-S-E motif (see, e.g., FIG. 3B). PARPs use the H-Y-E catalytic motif to deposit ADP-ribose to carboxylic acid acceptors. ADP-ribosyltransferases containing the R-S-E catalytic motif use the guanidino group as the acceptor.

Figure 4:
FIG. 4 shows domain architecture of PARP4. PARP4 is composed of a phosphopeptide binding module (BRCT), PARP catalytic domain, a vault protein inter-alpha trypsin (VIT) domain, a von Willebrand A (vWA) domain, a nuclear localization signal (NLS) and a major vault protein interaction (mINT) domain.

PARP4 is unique among ADP-ribosyltransferases because it contains a major vault protein interaction (mINT) domain at its C-terminus that binds to the vault (see, e.g., FIG. 4). To accommodate passenger molecules or passenger excipients with guanidino acceptor groups, the catalytic motif of PARP4 may be altered to R-S-E. Moreover, one or more domains within PARP4 may be exchanged, or one or more amino acids may be added, deleted or replaced.

ADP-ribosylation is a reversible post-translational modification that functions in multiple cellular pathways. Functionally, it may either prime the molecule for a specific function or it may silence or protect the molecule until it is delivered to the cell. Release of the ADP-ribosylated vault contents within the cell exposes the vault cargo to glycohydrolases such as poly ADP-ribose glycohydrolase (PARG), which enzymatically cleave the ADP-ribose to release the passenger molecule and/or return the passenger molecule to its original state.

Alternatively, passenger molecules may be accommodated within the internal cavity formed by the vault by using site directed mutagenesis to mutate, delete and/or insert one or more amino acids in the vault structure that enhance non-covalent interactions between the passenger molecule and the vault particle. To accommodate a negatively charged passenger molecule, e.g., DNA or RNA, one or more amino acids with a positively charged side chain, e.g., arginine (Arg, R) or lysine (Lys, K), will be introduced by mutation, deletion and/or insertion in the vault structure to increase the local positive charge (FIG. 10A) thereby enhancing electrostatic interaction between the passenger molecule and the vault (FIG. 10B). To accommodate a positively charged passenger molecule, one or more amino acids with a negatively charged side chain, e.g., aspartic acid (Asp, D) or glutamic acid (Glu, E), will be introduced by mutation, deletion and/or insertion in the vault structure to increase the local negative charge thereby enhancing electrostatic interaction between the passenger molecule and the vault. To accommodate a polar passenger molecule, one or more amino acids with a polar side chain, e.g., asparagine (Asn, N), cysteine (Cys, C), glutamine (Gin, Q), histidine (His, H), serine (Ser, S), threonine (Thr, T), tryptophan (Trp, W) or tyrosine (Tyr, Y), will be introduced by mutation, deletion and/or insertion to increase the local hydrophilicity thereby enhancing hydrophilic interactions between the passenger and the vault. To accommodate a non-polar passenger molecule, one or more amino acids with a hydrophobic side chain, e.g., alanine (Ala, A), glycine (Gly, G), isoleucine (Ile, I), leucine (Leu, L), methionine (Met, M), phenylalanine (Phe, F), proline (Pro, P), or valine (Val, V), will be introduced by mutation, deletion and/or insertion in the vault structure to increase the local hydrophobicity thereby enhancing hydrophobic interactions between the passenger molecule and the vault.

The vault particle contains three separate regions where the structure has not been solved by x-ray crystallography. One of the three unstructured regions is located in the shoulder region and is orientated to the outside of the vault particle (FIG. 11A). To target vaults to specific receptors or ligands, a targeting sequence can be inserted into the unstructured region or can replace the sequence comprising the unstructured region within the shoulder domain of the vault (FIG. 11B). Insertion of a targeting ligand within the unstructured shoulder domain promotes targeting of vaults to cells that express the receptor that recognizes the ligand (see, e.g., FIG. 12).

Compositions comprising vaults are described herein. In some embodiments, the compositions also comprise a passenger molecule. Methods to package smaller passenger molecules and alter physicomechanical properties of the vault particle are also described herein. Some methods described herein generally comprise ADP-ribose matrix formation. Methods to package hydrophobic molecules are also described herein. Methods to package charged molecules are also described herein. Methods to package polar molecules are also described herein. Some methods described herein generally comprise mutation, insertion or deletion of a specific amino acids in the vault structure. Methods to target the vault to specific receptors or ligands are also described herein.

Compositions

Provided herein are compositions that comprise a vault particle. Generally, the vault particles disclosed herein comprise a shell of MVP protein containing one or more engineered region comprised of one or more mutated or inserted amino acids. Generally, the vault particles disclosed herein comprise a cavity that is capable of binding a passenger molecule through non-covalent interactions, i.e., electrostatic interactions, hydrophobic interactions, and polar interactions (hydrogen bonding). Generally, the vault particles disclosed herein comprise an engineered region in the shoulder domain capable of binding to a specific binding partner.

Vault particles disclosed herein may comprise a shell (of MVP proteins), at least one vault-associated protein and an ADP-ribose matrix. In some instances, the passenger molecule is contained within the ADP-ribose matrix. In some instances, the passenger molecule is contained within the ADP-ribose matrix, but not attached to the ADP-ribose matrix. In some instances, the passenger molecule is contained within the ADP-ribose matrix, but not attached to the vault particle. In some instances, the passenger molecule is covalently attached to the ADP-ribose matrix. In some instances, the passenger molecule is free within the ADP-ribose matrix.

Generally, ADP-ribose matrices disclosed herein are the result of ADP-ribosylation. ADP-ribosylation within the vault confers new properties to the vault particle. First, addition of each ADP-ribose monomer contributes two negatively charged phosphate groups (see FIG. 2), which changes the electrostatic properties of the acceptor molecule. At the particle level, the overall change of electrostatic properties can alter the biodistribution, targeting, and cellular uptake of the vault particle. The degree of ADP-ribosylation, and hence the electrostatic changes, can be controlled by regulating the concentration of NAD+, the reaction time and the reaction temperature. Thus, by precisely regulating the degree of ADP-ribosylation within the vault complex different degrees of vault particle functionality can be achieved. For instance, addition of ADP-ribose inside the vault consumes empty space between enclosed molecules. Monomers or polymers of ADP-ribose create the ADP-ribose matrix that generates a turgor-like pressure on the vault particle walls, which increases the compressive and tensile strength of the vault, making it less deformable.

In some embodiments, the vault particle or a vault-associated protein is not connected to the passenger molecule. In some embodiments, the passenger molecule is located within the vault particle, but is not connected to the vault particle or vault-associated protein. In some embodiments, the vault particle or vault-associated protein does not possess a domain capable of connecting to the passenger molecule. In some embodiments, the vault particle or vault-associated protein does not possess a peptide capable of connecting to the passenger molecule. In some embodiments, the vault particle or vault-associated protein does not possess an amino acid capable of connecting to the passenger molecule. In some embodiments, the passenger molecule does not possess a feature capable of connecting to the vault particle or vault-associated protein. In some embodiments, the passenger molecule is not covalently connected to the vault particle or vault-associated protein. In some embodiments, the passenger molecule does not covalently interact with the vault particle or vault-associated protein. In some embodiments, the passenger molecule is free within the vault particle. In some embodiments, the passenger molecule is freely encapsulated by the vault during vault assembly. In some embodiments, the passenger molecule is fused to a C-terminus of the vault particle. In some embodiments, the passenger molecule is fused to an N-terminus of the vault nanoparticle. In some embodiments, the passenger molecule is fused to a mINT domain of the vault-associated protein. In some embodiments, the passenger molecule is not fused to a mINT domain of the vault-associated protein.

In some instances, the MVP or vault-associated protein is based on a wild type MVP or vault-associated protein, respectively. In some instances, at least one of the MVP and vault-associated protein comprises an amino acid substitution relative to a wild type MVP or vault-associated protein, respectively. In some instances, at least one of the MVP and vault-associated protein comprises an amino acid insertion relative to a wild type occurring MVP or vault-associated protein, respectively. In some instances, at least one of the MVP and vault-associated protein comprises an amino acid deletion relative to a wild type MVP or vault-associated protein, respectively. Such substitution, insertions, and deletions may be referred to herein as amino acid modifications.

In some embodiments, at least one of the MVP and vault-associated protein comprises an amino acid modification resulting in a mutation of a wild type amino acid to an amino acid that has a charged side chain, e.g., arginine (Arg, R), aspartic acid (Asp, D), glutamic acid (Glu, E) or lysine (Lys, K). In some embodiments, one or more amino acids with a charged side group, e.g., arginine (Arg, R), aspartic acid (Asp, D), glutamic acid (Glu, E) or lysine (Lys, K) are inserted into an inner-facing surface. In some embodiments, the mutations and/or insertions result in a local, spatially clustered negative charge in the engineered region. In some embodiments, the mutations and/or insertions result in a local, spatially clustered positive charge in the engineered region. In some embodiments, the passenger molecule non-covalently binds to the negatively charged engineered region. In some embodiments, the passenger molecule non-covalently binds to the positively charged engineered region. In some embodiments, the passenger molecule is a DNA or a RNA molecule. In some embodiments, the passenger molecule is a protein or peptide molecule. In some embodiments, the passenger molecule is a small molecule.

In some embodiments, at least one of the MVP and vault-associated protein comprises an amino acid modification resulting in a mutation of an amino acid to an amino acid that has a hydrophobic side chain, e.g., alanine (Ala, A), glycine (Gly, G), isoleucine (Ile, I), leucine (Leu, L), methionine (Met, M), phenylalanine (Phe, F), proline (Pro. P), or valine (Val, V). In some embodiments, one or more amino acids with a hydrophobic side group, e.g., alanine (Ala, A), glycine (Gly, G), isoleucine (Ile. I), leucine (Leu, L), methionine (Met, M), phenylalanine (Phe, F), proline (Pro, P), or valine (Val, V) are inserted into an inner-facing surface. In some embodiments, the mutations and/or insertions result in a local, spatially clustered hydrophobic patch. In some embodiments, the passenger molecule non-covalently binds to the engineered hydrophobic patch. In some embodiments, the passenger molecule is a DNA or a RNA molecule. In some embodiments, the passenger molecule is a protein or peptide molecule. In some embodiments, the passenger molecule is a small molecule.

In some embodiments, at least one of the MVP and vault-associated protein comprises an amino acid modification resulting in a mutation of an amino acid to an amino acid that has a polar side chain, e.g., asparagine (Asn, N), cysteine (Cys, C), glutamine (Gln, Q), histidine (His, H), serine (Ser, S), threonine (Thr, T), tryptophan (Trp, W) or tyrosine (Tyr, Y). In some embodiments, one or more amino acids with a polar side group, e.g., asparagine (Asn, N), cysteine (Cys, C), glutamine (Gln, Q), histidine (His, H), serine (Ser, S), threonine (Thr, T), tryptophan (Trp, W) or tyrosine (Tyr, Y) are inserted into an inner-facing surface. In some embodiments, the mutations and/or insertions result in a local, spatially clustered polar patch capable of hydrogen bonding. In some embodiments, the passenger molecule non-covalently binds to the engineered polar patch. In some embodiments, the passenger molecule is a DNA or a RNA molecule. In some embodiments, the passenger molecule is a protein or peptide molecule. In some embodiments, the passenger molecule is a small molecule.

In some instances, vault particles disclosed herein comprise at least one amino acid modification in the interior of the vault particle that results in non-covalent binding of a passenger molecule to the interior of the vault particle. Non-covalent binding may occur through an electrostatic interaction. Non-covalent binding may occur through a hydrophobic interaction. Non-covalent binding may occur through a polar interaction. The modification may comprise a specific amino acid sequence. The modification may comprise a non-specific amino acid sequence. The modification may comprise a modification of a motif or domains described herein.

Amino acid sequences, motifs and domains may comprise a modification allowing a passenger molecule, such as a nucleic acid, a protein, or a small molecule, to bind specifically or non-specifically, through at least one of an electrostatic interaction, a hydrophobic interaction and a polar interaction. By way of non-limiting example, electrostatic interactions between amino acids with positively charged side groups, e.g., arginine (Arg, R) and lysine (Lys, K), may promote binding with negatively charged molecules such as phosphate groups found within nucleic acids and amino acids with negatively charged side groups, e.g., aspartic acid (Asp, D) und glutamic acid (Gla, E), found within peptides or proteins. Similarly, hydrophobic interactions between hydrophobic amino acids, e.g., alanine (Ala, A), glycine (Gly, G), isoleucine (Ile, I), leucine (Lea, L), methionine (Met, M), phenylalanine (Phe, F), proline (Pro, P), and valine (Val, V) may promote binding to hydrophobic nitrogenous bases found within nucleic acids, hydrophobic small molecules and to complementary hydrophobic amino acids in proteins and peptides of passenger molecules. Polar interactions, leading to hydrogen bonding, between polar amino acids, e.g., asparagine (Asn, N), cysteine (Cys, C), glutamine (Gln, Q), histidine (His, H), serine (Ser, S), threonine (Thr, T), tryptophan (Trp, W) and tyrosine (Tyr, Y), as well as charged amino acids, may promote binding to nitrogenous bases in passenger molecules, such as nucleic acids, polar small molecules and to other polar amino acids in proteins and peptides.

In some instances, amino acid modifications are located on a loop that faces an internal vault particle cavity. In some instances, amino acid modifications are located on a side chain that faces an internal vault particle cavity. Loops and side chains, based on the crystal structures such as those described herein, that face the internal vault particle cavity may be key sites (FIG. 10A) for the mutation or insertion of charged, hydrophobic or polar amino acids to create discrete areas or patches for binding passenger molecules. In some instances, two or more amino acid modifications are spatially adjacent. In some instances, two or more amino acid modifications are sequentially adjacent. In some instances, a single site may not have the binding strength alone to immobilize a passenger molecule. In some instances, a single amino acid modification may not have the binding strength alone to immobilize a passenger molecule. In some instances, a combination of sites has the binding strength to immobilize a passenger molecule. In some instances, a combination of amino acids resulting from amino acid modifications has the binding strength to immobilize a passenger molecule. In some instances, an MVP chain comprises a plurality of amino acid modifications. In some instances, each of the MVP chains comprises an amino acid modification, as exemplified by FIG. 10A. The passenger molecule may become sufficiently "tacked" to the internal cavity of the vault particle throughout the entire vault structure (FIG. 10B).

In some instances, vault particles disclosed herein comprise a shell of MVP protein and a peptide inserted within a shoulder domain of the MVP. In some instances, the shoulder domain is an engineered shoulder domain that is capable of specific binding to receptors or ligands expressed on cells. In some instances, the shoulder domain is capable of binding to receptor or ligands not expressed on cells.

In some instances, an amino acid modification is present on an outer facing domain of the major vault protein, wherein the outer facing domain is a shoulder domain. In some instances, the outer facing domain is flexible as compared to surrounding domains that are more rigid. In some instances, domains that are more rigid comprise at least one secondary protein structure, such as an alpha helix or beta strand. In some instances, domains that are more rigid comprise at least one tertiary protein structure, such as an alpha helix or beta strand. In some instances, domains that are flexible comprise a loop region. In some instances, domains that are flexible do not comprise a secondary or tertiary protein structure. By way of non-limiting example, the crystal structure of the rat vault particle reveals an outer-facing region is present within the shoulder domain and extends from Met608 to Pro620 for which the structure has not been solved (FIG. 11A). The unstructured nature of this region indicates that the chain is flexible and may accommodate an addition to or complete replacement of the intervening sequence providing an opportunity to insert a peptide for targeting the vault particle to specific cells. By inserting the peptide into the flexible region of the shoulder domain, the peptide may be anchored by amino acids flanking the flexible region, which are structured by the formation of an alpha helix and a beta strand (see FIG. 11A). In addition, insertion of a peptide into the shoulder domain may evenly distribute the peptide along a circumference of about 1256.6 Å as opposed to a maximum circumference of 157 Å at the cap-ring, making more of it available to a target cell.

Vault-Associated Proteins

Generally, compositions disclosed herein comprise a vault particle and a vault-associated protein. In some embodiments, the vault-associated protein comprises a major vault protein interaction domain that provides for an interaction between the vault-associated protein and a major vault protein. In some embodiments, the vault-associated protein comprises a poly-adenosine diphosphate (ADP)-ribose polymerase (referred to herein as a "PARP"). In some embodiments, the vault-associated protein consists essentially of a PARP. In some embodiments, the PARP is PARP4, also known in the field as vault PARP (VPARP). In some embodiments, the vault-associated protein comprises an arginine specific ADP-ribosyltransferses (ART). In some embodiments, the vault-associated protein consists essentially of an ART. In some embodiments, the vault-associated protein comprises a member of the poly (A) polymerase family. In some embodiments, the vault-associated protein comprises a glycosyltransferase. In some embodiments, the vault-associated protein comprises a fatty acid synthase. In some embodiments, the vault-associated protein comprises a farnesyltransferase. In some embodiments, the vault-associated protein is an enzyme that catalyzes the formation of a polymer. In some embodiments, the enzyme is passively encapsulated by the vault particle. In some embodiments, the enzyme is passively encapsulated during vault assembly in an in vitro cell-free protein expression system. In some embodiments, the enzyme is associated with the vault after vault assembly in an in vitro cell-free protein expression system. In some embodiments, the enzyme is associated with the vault after vault assembly in a cell-based protein expression system. In some embodiments, the enzyme is attached to the mINT domain of PARP4. For each enzyme, a different substrate is required, thus the resulting matrix may be dependent on the enzyme and substrate.

In some embodiments, the PARP protein comprises an amino acid sequence for a PARP. In some embodiments, the PARP protein consists essentially of an amino acid sequence for a PARP. In some embodiments, the PARP protein comprises an amino acid sequence for PARP4. In some embodiments, the PARP4 protein consists essentially of an amino acid sequence for PARP4. A person skilled in the art understands that due to population variation, there are many amino acid sequences for PARP4. However, non-limiting examples of PARP4 proteins are NCBI GenBank XP 011533233.1, NCBI GenBank XP_011533234.1, and NCBI GenBank NP_006428.2 (SEQ ID NO.: 2, see Table 1)

In some embodiments, the PARP4 protein is represented by SEQ ID NO.: 2. In some embodiments, the PARP4 protein is represented by a sequence that is at least about 95% homologous to SEQ ID NO.: 2. In some embodiments, the PARP4 protein is represented by a sequence that is at least about 90% homologous to SEQ ID NO.: 2. In some embodiments, the PARP4 protein is represented by a sequence that is at least about 85% homologous to SEQ ID NO.: 2. In some embodiments, the PARP4 protein is represented by a sequence that is at least about 80% homologous to SEQ ID NO.: 2. In some embodiments, the PARP4 protein is represented by a sequence that is at least about 75% homologous to SEQ ID NO.: 2.

In some embodiments, the PARP4 protein is encoded by SEQ ID NO.: 1 (see Table 1). In some embodiments, the PARP4 protein is encoded by a sequence that is at least about 95% homologous to SEQ ID NO.: 1. In some embodiments, the PARP4 protein is encoded by a sequence that is at least about 90% homologous to SEQ ID NO.: 1. In some embodiments, the PARP4 protein is encoded by a sequence that is at least about 85% homologous to SEQ ID NO.: 1. In some embodiments, the PARP4 protein is encoded by a sequence that is at least about 80% homologous to SEQ ID NO.: 1. In some embodiments, the PARP4 protein is encoded by a sequence that is at least about 75% homologous to SEQ ID NO.: 1.

In some embodiments, the PARP protein comprises a modified PARP protein comprising an amino acid sequence that has been modified from a wild type amino acid sequence for a PARP. In some embodiments, the modified PARP protein is referred to herein as an engineered variant of the PARP. In some embodiments, the PARP protein contains at least one modified amino acid in one or more domains or one or more motifs of the PARP. In some embodiments, the domain or motif is selected from a phosphopeptide binding module (BRCT), a PARP catalytic domain, a vault protein inter-alpha trypsin (VIT) domain, a von Willebrand A (vWA) domain, a nuclear localization signal (NLS) and a major vault protein interaction (mINT) domain. Methods of modifying protein sequences are well known in the art, and include modifying a nucleic acid encoding the protein sequence. In some embodiments, the modified PARP protein is capable of performing at least one activity performed by unmodified PARP protein. In some embodiments, the modified PARP protein is capable of performing the at least one activity better than the unmodified PARP protein. In some embodiments, the modified PARP protein is not capable of performing the at least one activity as well as the unmodified PARP protein.

In some embodiments, the modified PARP protein comprises a deletion of at least one amino acid relative to an unmodified PARP protein. In some embodiments, the modified PARP protein comprises a substitution of at least one amino acid relative to an unmodified PARP protein. In some embodiments, the modified PARP protein comprises an addition of at least one amino acid relative to an unmodified PARP protein.

In some embodiments, the vault-associated protein is a telomerase-associated protein. In some embodiments, the telomerase-associated protein is telomerase-associated protein 1 (TEP1).

In some embodiments, compositions comprise the vault particle, a telomerase-associated protein and a PARP. In some embodiments, compositions comprise the vault particle, TEP1 and PARP4.

Additional Vault Components

Compositions disclosed herein may comprise additional vault components beyond the major vault protein and vault associated protein. In some embodiments, the vault particle comprises a non-coding vault ribonucleic acid (vtRNA). vtRNA has been well described by those in the field. Briefly, vtRNA generally has a length of about 80 to about 150 bases, depending on the species of origin. Non-limiting examples of human vtRNA include hvg1 (98 bases), hvg2 (88 bases), and hvg3 (88 bases). vtRNAs may have secondary structures selected from, but not limited to, arches, hollow barrel-like frameworks, and stem loops. The stem loops may connect the 5' and 3' ends of the vtRNA. Thus, vtRNAs are capable of siRNA activity.

Figure 8:
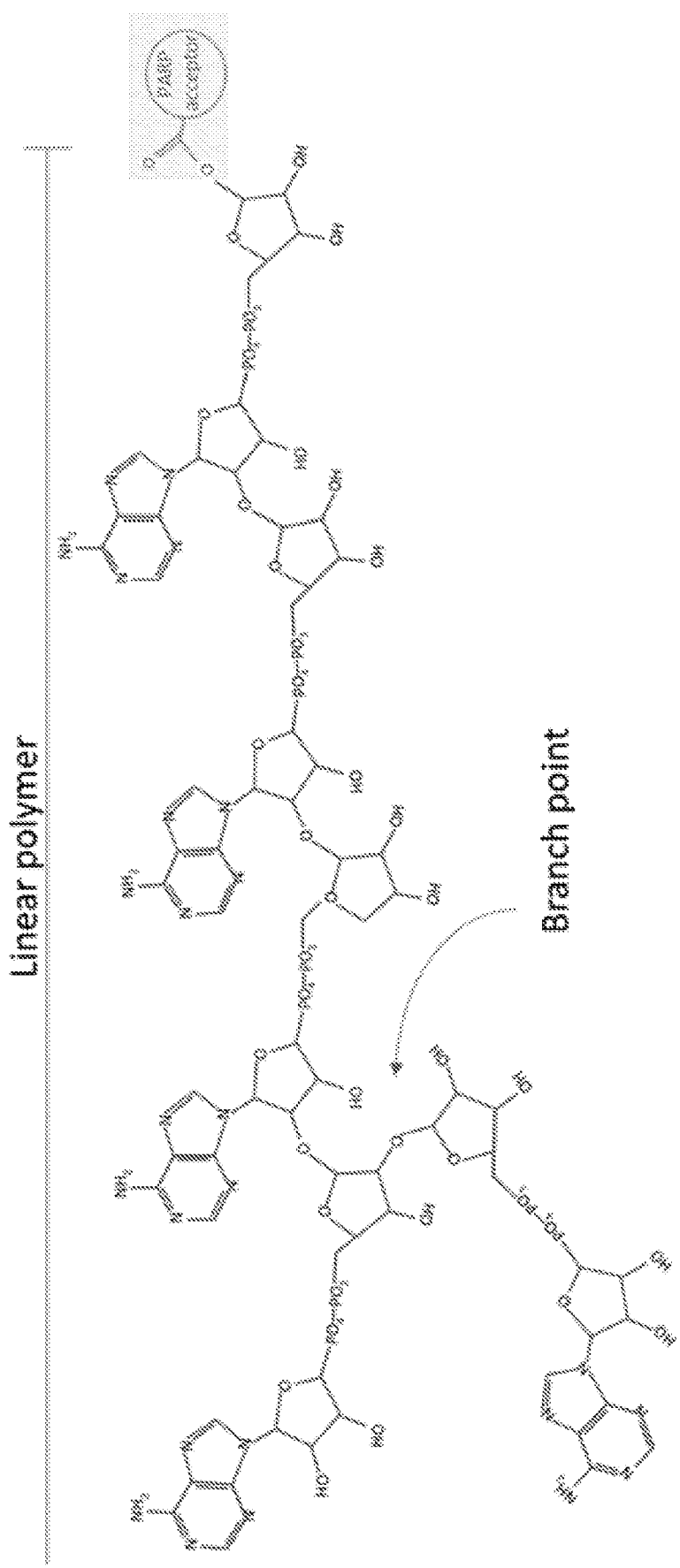
FIG. 8 shows an exemplary linear and branched ADP ribose polymer.

In some embodiments, the vault particle comprises an ADP-ribose matrix. In some embodiments, an ADP-ribose matrix is composed of ADP-ribose monomers, each monomer occupying an approximate volume of about 0.6 nm$^3$ to about 1.5 nm$^3$. In some embodiments, an ADP-ribose matrix is composed of polymers formed by the addition of ADP-ribose in a linear fashion. In some embodiments, an ADP-ribose matrix is composed of polymers formed by the addition of ADP-ribose in a linear and branched fashion. In some embodiments, an ADP-ribose matrix is composed of a combination of ADP-ribose monomers and linear and/or branched ADP-ribose polymers. In some embodiments, the ADP-ribose matrix is composed of about 1,000 to about 55,000 ADP-ribose monomers and linear and/or branched ADP-ribose polymers. In some embodiments, the ADP-ribose matrix is composed of about 1,000 to about 5,000 ADP-ribose monomers and linear and/or branched ADP-ribose polymers. In some embodiments, the ADP-ribose matrix is composed of about 5,000 to about 10,000 ADP-ribose monomers and linear and/or branched ADP-ribose polymers. In some embodiments, the ADP-ribose matrix is composed of about 10,000 to about 50,000 ADP-ribose monomers and linear and/or branched ADP-ribose polymers. FIG. 8 illustrates exemplary linear and/or branched ADP-ribose polymers. In some embodiments, the ADP-ribose matrix is formed by contacting a vault particle with oxidized nicotinamide adenine dinucleotide (NAD+) to produce a dense matrix of ADP-ribose monomers and/or polymers. In some embodiments, the ADP-ribose matrix is formed by contacting a vault particle with an analog of NAD+. Non-limiting examples analogs of NAD+ include oxidized forms of: nicotinamide 1,$N^6$-ethenoadenine dinucleotide, nicotinamide guanine dinucleotide, nicotinamide hypoxanthine dinucleotide, and nicotinamide hypoxanthine dinucleotide.

In some embodiments, compositions comprise an acceptor site for ADP-ribosylation. In some embodiments, the acceptor site is located on a passenger molecule of interest. In some embodiments, the acceptor site is located on an excipient passenger molecule. In some embodiments, the acceptor site is NAD+ or an NAD+ analog. In some embodiments, the acceptor site is located on the MVP. In some embodiments, the acceptor site is located on the vault-associated protein. In some embodiments, the acceptor site is located on a PARP4, wherein the PARP4 is associated with the vault particle of the composition. In some embodiments, the PARP4 is an engineered variant of PARP4.

In some embodiments, the passenger molecule comprises an acceptor site for ADP-ribose. In some embodiments, the method comprises contacting a vault protein of the vault particle with an excipient molecule that has an acceptor site for ADP-ribose. In some embodiments, a vault protein of the vault particle comprises an acceptor for ADP-ribose.

In some embodiments, the compositions disclosed herein comprise a cofactor to enhance matrix formation and stability. Non-limiting examples of cofactors include calcium, or other multivalent cations, and ATP. In some embodiments, the composition comprises a lipid (not as a passenger molecule), wherein the lipid alters the physicomechanical properties of the vault.

Passenger Molecules

In some embodiments, the compositions disclosed herein comprise a passenger molecule. In some embodiments, the passenger molecule is trapped within the ADP-ribose matrix within the cavity of the vault. In some embodiments, the passenger molecule would otherwise readily diffuse out of the vault particle if it was not trapped. In some embodiments, the passenger molecule is too large to diffuse out of the cavity of the vault particle. In some embodiments, the passenger molecule is too large to diffuse out of the ADP-ribose matrix within the cavity of the vault.

In some embodiments, the compositions disclosed herein comprise a PARP protein, an ADP-ribose matrix, and a passenger molecule that is large enough to be retained within the vault cavity (e.g., too big to diffuse out of the vault complex). In some embodiments, the compositions disclosed herein comprise a PARP protein, an ADP-ribose matrix, and a passenger molecule that is trapped in the cavity by the ADP-ribose matrix.

Non-limiting examples of passenger molecules include peptides (generally less than 100 amino acids), proteins, carbohydrates, nucleic acids, lipids, small molecules (molecules generally less than 900 daltons), and active pharmaceutical ingredients. In some embodiments, the passenger molecule is selected from a peptide, a protein, a carbohydrate, a nucleic acid, a lipid, a small molecule, an active pharmaceutical ingredient, and a combination thereof.

The passenger molecule may have a molecular weight between about 100 daltons and about 10 mega daltons. The passenger molecule may have a molecular weight between about 100 daltons and about 900 daltons. The passenger molecule may have a molecular weight between about 100 daltons and about 900 daltons. The passenger molecule may have a molecular weight between about 900 daltons and about 90,000 daltons. The passenger molecule may have a molecular weight that is less than about 1000 daltons. The passenger molecule may have a molecular weight that is less than about 900 daltons. The passenger molecule may have a molecular weight that is less than about 800 daltons. The passenger molecule may have a molecular weight that is less than about 700 daltons. The passenger molecule may have a molecular weight that is less than about 600 daltons. The passenger molecule may have a molecular weight that is less than about 500 daltons. The passenger molecule may have a molecular weight that is greater than about 900 daltons. The passenger molecule may have a molecular weight that is greater than about 500 daltons. The passenger molecule may have a molecular weight that is greater than about 900 daltons. The passenger molecule may have a molecular weight that is greater than about 1000 daltons. The passenger molecule may have a molecular weight that is greater than about 1200 daltons. The passenger molecule may have a molecular weight that is greater than about 1500 daltons.

Methods of Producing Vault Particles

Provided herein are methods for producing a vault particle, wherein the methods comprise ADP-ribosylation of a vault enclosed passenger molecule resulting in an ADP-ribose matrix that immobilizes the vault-enclosed passenger molecule. In some embodiments. ADP-ribosylation of a vault enclosed passenger molecule occurs following synthesis of a vault particle in an in vitro cell-free protein expression system. In some embodiments, ADP-ribosylation of a vault enclosed passenger molecule occurs following synthesis of a vault particle in a cell-based protein expression system.

In some embodiment, the ADP-ribosylation is catalyzed by a PARP. In some embodiment, the ADP-ribosylation is catalyzed by PARP4. In some embodiments, the ADP-ribosylation is catalyzed by an ART. In some embodiments, methods comprise use of NAD+ or an NAD+ analog as a substrate for ADP-ribosylation. Methods disclosed herein may also be referred to as a "reaction."

In some embodiments, methods comprise immobilizing passenger molecules by incubating nicotinamide adenine dinucleotide (NAD+) or NAD+ analogs and the enzyme PARP4 or engineered PARP4 variants to create a dense matrix of ADP-ribose monomers and/or polymers.

In some embodiments, method comprise labeling passenger molecules with ADP-ribose, monomers and/or polymers, derived from the substrate NAD+ or NAD+ analogs and catalyzed by the PARP4 enzyme or engineered PARP4 variants.

In some embodiments, methods comprise enclosing the passenger molecule in the vault while producing the vault particle. In some embodiments, methods comprise enclosing the passenger molecule in the vault after producing the vault particle.

In some embodiments, the methods comprise incubating a vault-associated protein with a vault prior to the addition of a substrate (e.g., NAD+) or passenger molecule to be contained within the vault particle. In some embodiments, PARP4, or an engineered PARP4 variant, is incubated with a vault that contains the passenger molecule, before a substrate is added.

In some embodiments, methods comprise adding about 0.1 µM to about 20 mM of the substrate (e.g., NAD+, or analog thereof) to the vault-associated protein. In some embodiments, methods comprise adding about 0.1 µM to about 1 µM of the substrate to the vault-associated protein. In some embodiments, methods comprise adding about 1 µM to about 10 µM of the substrate to the vault-associated protein. In some embodiments, methods comprise adding about 10 µM to about 100 µM of the substrate to the vault-associated protein. In some embodiments, methods comprise adding about 0.1 mM to about 1 mM of the substrate to the vault-associated protein. In some embodiments, methods comprise adding about 1 mM to about 10 mM of the substrate to the vault-associated protein. In some embodiments, methods comprise adding about 10 mM to about 20 mM of the substrate to the vault-associated protein.

In some embodiments, the reaction has a duration. The duration may be defined as the time that the substrate is added to the vault-associated protein until the time that an ADP ribose matrix is formed. The duration may be defined as the time that the substrate is added to the vault-associated protein until the time an ADP ribose matrix is formed, wherein the ADP ribose matrix formed has select properties (e.g., density, compressive strength, stability, electrostatic properties). In some embodiments, the duration is about 5 minutes to about 24 hours. In some embodiments, the duration is about 5 minutes to about 10 minutes. In some embodiments, the duration is about 5 minutes to about 30 minutes. In some embodiments, the duration is about 30 minutes to about 1 hour. In some embodiments, the duration is about 1 hour to about 4 hours. In some embodiments, the duration is about 4 hours to about 8 hours. In some embodiments, the duration is about 8 hours to about 12 hours. In some embodiments, the duration is about 12 hours to about 18 hours. In some embodiments, the duration is about 18 hours to about 24 hours.

In some embodiments, the methods comprise incubating a vault-associated protein, vault and substrate in a buffered solution. The buffered solution may be a Tris buffer. In some embodiments, the concentration of Tris buffer in the buffered solution is about 10 mM to about 100 mM. In some embodiments, the concentration of Tris buffer in the buffered solution is about 10 mM to about 20 mM. In some embodiments, the concentration of Tris buffer in the buffered solution is about 20 mM to about 30 mM. In some embodiments, the concentration of Tris buffer in the buffered solution is about 30 mM to about 40 mM. In some embodiments, the concentration of Tris buffer in the buffered solution is about 40 mM to about 50 mM. In some embodiments, the concentration of Tris buffer in the buffered solution is about 50 mM to about 60 mM. In some embodiments, the concentration of Tris buffer in the buffered solution is about 60 mM to about 70 mM. In some embodiments, the concentration of Tris buffer in the buffered solution is about 70 mM to about 80 mM. In some embodiments, the concentration of Tris buffer in the buffered solution is about 80 mM to about 90 mM. In some embodiments, the concentration of Tris buffer in the buffered solution is about 90 mM to about 100 mM.

In some embodiments, the reaction occurs at about 20° C. to about 37° C. In some embodiments, the reaction occurs at about 20° C. In some embodiments, the reaction occurs at about 25° C. In some embodiments, the reaction occurs at about 37° C.

In some embodiments, the vault particle is synthesized using an in vitro cell-free protein expression system. In some embodiments, the vault particle is synthesized in a cell-based protein expression system.

Further provided herein are methods for ADP-ribosylation of a vault enclosed passenger molecule, wherein ADP-ribosylation is catalyzed by a vault-associated protein and results in an ADP-ribose matrix that traps the passenger molecule. In some embodiments, the vault-associated protein is a PARP. In some embodiments, the vault-associated protein is PARP4 or an engineered variant of PARP4.

In some embodiments, methods comprise altering the physicomechanical properties of the vault particle. In some embodiments, methods comprise adding cofactors, such as $Ca^{2+}$ or ATP, to alter the physicomechanical properties of the vault particle. In some embodiments, methods comprise adding a lipid molecule to alter the physicomechanical properties of the vault particle.

In some embodiments, production of ADP-ribose monomers and/or polymers (resulting from ADP-ribosylation) alters the density of the content of the vault particle. In some embodiments, addition of ADP-ribose monomers and/or polymers alters the electrostatic properties of the vault particle. In some embodiments, addition of ADP-ribose monomers and/or polymers strengthens the vault particle against compression. In some embodiments, addition of ADP-ribose monomers and/or polymers stabilizes the vault particle. In some embodiments, calcium ions, or other multivalent cations, and/or ATP act as cofactors to enhance matrix formation and stability. In some embodiments, lipids are added to alter the physicomechanical properties of the vault. In some embodiments, immobilization of passenger molecules in the ADP-ribose matrix enhances their delivery to a cell.

In some embodiments, immobilization of passenger molecules in the ADP-ribose matrix enhances their delivery to the nucleus of a cell. ADP-ribose matrix within the vault may play an important role in the delivery of the enclosed passenger molecules to the cell. The ADP-ribose matrix may promote nuclear transport of the passenger molecules from the vault interior. The association of the vault with the nuclear pore might induce the opening of the vault cap(s), and the difference in osmotic pressure between the cytoplasm and the nucleus will induce expulsion of the ADP-ribose matrix with its content from the vault particle into the nucleus.

In some embodiments, methods comprise fusing the passenger molecule to a carboxyl-terminus of the vault particle, also referred to as the cap of the vault, see, e.g., FIG. 1A. In some embodiments, methods comprise fusing the passenger molecule to an amino-terminus of the vault nanoparticle, also referred to as the waist of the vault see, e.g., FIG. 1B.

Provided herein are methods for producing a vault particle, wherein the methods comprise sequence and structural analysis, site-directed mutagenesis and cloning resulting in an engineered vault that contains multiple non-covalent binding regions. In some embodiments, an engineered vault particle is synthesized in an in vitro cell-free protein expression system. In some embodiments, an engineered vault particle is synthesized in a cell-based protein expression system.

In some embodiments, the inner-facing loops and chains contain one or more charged, hydrophobic or polar amino acids and additional like amino acids are introduced by mutation of sequence adjacent or spatially adjacent amino acids. In some embodiments, the inner-facing loops and chains do not contain one or more charged, hydrophobic or polar amino acids and additional like amino acids are introduced by mutation of sequence adjacent or spatially adjacent amino acids.

In some embodiments, the inner-facing loops and chains contain one or more charged, hydrophobic or polar amino acids and additional like amino acids are introduced by insertion of sequence adjacent or spatially adjacent amino acids. In some embodiments, the inner-facing loops and chains do not contain one or more charged, hydrophobic or polar amino acids and additional like amino acids are introduced by insertion of sequence adjacent or spatially adjacent amino acids. In some embodiments, about one to about 10 amino acids are inserted. In some embodiments, about 10 to about 50 amino acids are inserted. In some embodiments, about 50 to about 100 amino acids are inserted. In some embodiments, about 100 to about 200 amino acids are inserted. In some embodiments, about 200 to about 300 amino acids are inserted.

In some embodiments, the amino acid sequence inserted into the unstructured region of the shoulder domain results in a receptor binding peptide. In some embodiments, the amino acid sequence inserted into the shoulder domain results in a ligand binding peptide. In some embodiments, the amino acid sequence inserted into the unstructured region of the shoulder domain results in a receptor binding peptide that binds a receptor expressed by a cell. In some embodiments, the amino acid sequence inserted into the unstructured region of the shoulder domain results in a ligand binding peptide that binds a ligand expressed by a cell. In some embodiments, the amino acid sequence inserted into the unstructured region of the shoulder domain results in a receptor binding peptide that binds receptor not expressed by a cell. In some embodiments, the amino acid sequence inserted into the unstructured region of the shoulder domain results in a ligand binding peptide that binds a ligand not expressed by a cell.

In some embodiments, the inserted peptide is composed of about 2 to about 10 amino acids. In some embodiments, the inserted peptide is composed of about 10 to about 50 amino acids. In some embodiments, the inserted peptide is composed of about 50 to about 100 amino acids. In some embodiments, the inserted peptide is composed of about 100 to about 200 amino acids. In some embodiments, the inserted peptide is composed of about 200 to about 500 amino acids. In some embodiments, the amino acids within the unstructured region of the shoulder domain are retained. In some embodiments, the amino acids within the unstructured region of the shoulder domain are removed.

Uses of Vault Particles and Methods of Treatment

Provided herein are methods that comprise delivering a vault particle to a cell, wherein the vault particle comprises an enclosed, immobilized passenger molecule within a matrix of ADP-ribose. In some embodiments, the vault particle localizes to the nucleus of the cell. Further provided herein are methods of treating a condition in a subject in need thereof, comprising administering a vault particle to the subject. In some instances, the vault particle comprises an enclosed, immobilized passenger molecule within a matrix of ADP-ribose. In some instances, the vault particle comprises an enclosed passenger molecule non-covalently bound to the inner surface of the vault cavity.

In some embodiments, the cell or subject is affected by a disease or condition. Non-limiting examples of diseases and conditions are autoimmune diseases (e.g., arthritis), metabolic diseases (e.g., diabetes, cardiovascular disease), neurological conditions (e.g., Alzheimer's Disease, Parkinson's Disease, multiple sclerosis), and cancers (e.g., solid tumors, leukemias).

In some embodiments, the cell is a cancer cell. In some embodiments, the cell is affected by a cancer. In some embodiments, the cell comprises a genetic mutation due to a cancer. In some embodiments, the cancer cell originates from a cancer.

In some instances, methods comprise delivering a vault particle to a cell, the vault particle comprising one or more engineered regions, wherein the engineered region is achieved by introducing a mutation to a region of a vault particle protein of the particle, and wherein the mutation increases a non-covalent binding property of the region. Non-limiting examples of non-covalent binding properties are electrostatic interactions, hydrophobic interactions, and polar interactions.

In some instances, methods comprise delivering a vault particle to cell, wherein the vault particle comprises a major vault protein and a peptide inserted in an unstructured region of a shoulder domain of the major vault protein. In some embodiments, the peptide is a non-engineered peptide. In some embodiments, the peptide is an engineered peptide. In some embodiments, the peptide is synthetic. In some embodiments, the peptide is at least a portion of a receptor that has affinity for a ligand. In some embodiments, the peptide is at least a portion of a ligand that has affinity for a receptor. In some embodiments, the vault particle comprises an engineered peptide from a receptor or ligand and comprises a passenger molecule. In some embodiments, the vault particle localizes to the nucleus of the cell.

TABLE 1

Exemplary human PARP4 Nucleic acid and Amino acid Sequences

| SEQ ID NO | Sequence |
|---|---|
| 1 | ATGGTGATGGGAATCTTTGCAAATTGTATCTTCTGTTTGAAAGTGAAGTACTTACCTC<br>AGCAGCAGAAGAAAAAGCTACAAACTGACATTAAGGAAAATGGCGGAAAGTTTTCC<br>TTTTCGTTAAATCCTCAGTGCACACATATAATCTTAGATAATGCTGATGTTCTGAGTC<br>AGTACCAACTGAATTCTATCCAAAAGAACCACGTTCATATTGCAAACCCAGATTTTA<br>TATGGAAATCTATCAGGGAAAAGAGACTCTTGGATGTAAAGAATTATGATCCTTATA<br>AGCCCCTGGACATCACACCACCTCCTGATCAGAAGGCGAGCAGTTCTGAAGTGAAA<br>ACAGAAGGTCTATGCCCGGACAGTGCCACAGAGGAGGAAGACACTGTGGAACTCAC<br>TGAGTTTGGTATGCAGAATGTTGAAATTCCTCATCTTCCTCAAGATTTTGAAGTTGCA<br>AAATATAACACCTTGGAGAAAGTGGGAATGGAGGGAGGCCAGGAAGCTGTGGTGGT<br>GGAGCTTCAGTGTTCGCGGGACTCCAGGGACTGTCCTTTCCTGATATCCTCACACTTC<br>CTCCTGGATGATGGCATGGAGACTAGAAGACAGTTTGCTATAAAGAAAACCTCTGA<br>AGATGCAAGTGAATACTTTGAAAATTACATTGAAGAACTGAAGAAACAAGGATTTC<br>TACTAAGAGAACATTTCACACCTGAAGCAACCCAATTAGCATCTGAACAATTGCAAG<br>CATTGCTTTTGGAGGAAGTCATGAATTCAAGCACTCTGAGCCAAGAGGTGAGCGATT<br>TAGTAGAGATGATTTGGGCAGAGGCCCTGGGCCACCTGGAACACATGCTTCTCAAGC |

TABLE 1-continued

Exemplary human PARP4 Nucleic acid and Amino acid Sequences

| SEQ ID NO | Sequence |
|---|---|
| | CAGTGAACAGGATTAGCCTCAACGATGTGAGCAAGGCAGAGGGGATTCTCCTTCTA
GTAAAGGCAGCACTGAAAAATGGAGAAACAGCAGAGCAATTGCAAAAGATGATGA
CAGAGTTTTACAGACTGATACCTCACAAAGGCACAATGCCCAAAGAAGTGAACCTG
GGACTATTGGCTAAGAAAGCAGACCTCTGCCAGCTAATAAGAGACATGGTTAATGT
CTGTGAAACTAATTTGTCCAAACCCAACCCACCATCCCTGGCCAAATACCGAGCTTT
GAGGTGCAAAATTGAGCATGTTGAACAGAATACTGAAGAATTTCTCAGGGTTAGAA
AAGAGGTTTTGCAGAATCATCACAGTAAGAGCCCAGTGGATGTCTTGCAGATATTTA
GAGTTGGCAGAGTGAATGAAACCACAGAGTTTTTGAGCAAACTTGGTAATGTGAGG
CCCTTGTTGCATGGTTCTCCTGTACAAAACATCGTGGGAATCTTGTGTCGAGGGTTGC
TTTTACCCAAAGTAGTGGAAGATCGTGGTGTGCAAAGAACAGACGTCGGAAACCTT
GGAAGTGGGATTTATTTCAGTGATTCGCTCAGTACAAGTATCAAGTACTCACACCCG
GGAGAGACAGATGGCACCAGACTCCTGCTCATTTGTGACGTAGCCCTCGGAAAGTGT
ATGGACTTACATGAGAAGGACTTTTCCTTAACTGAAGCACCACCAGGCTACGACAGT
GTGCATGGAGTTTCGCAAACAGCCTCTGTCACCACAGACTTTGAGGATGATGAATTT
GTTGTCTATAAAACCAATCAGGTTAAAATGAAATATATTATTAAATTTTCCATGCCTG
GAGATCAGATAAAGGACTTTCATCCTAGTGATCATACTGAATTAGAGGAATACAGAC
CTGAGTTTTCAAATTTTTCAAAGGTTGAAGATTACCAGTTACCAGATGCCAAAACTT
CCAGCAGCACCAAGGCCGGCCTCCAGGATGCCTCTGGGAACTTGGTTCCTCTGGAGG
ATGTCCACATCAAAGGGAGAATCATAGACACTGTAGCCCAGGTCATTGTTTTTCAGA
CATACACAAATAAAGTCACGTGCCCATTGAGGCAAAATATATCTTTCCTTTGGATG
ACAAGGCCGCTGTGTGTGGCTTCGAAGCCTTCATCAATGGGAAGCACATAGTTGGAG
AGATTAAAGAGAAGGAAGAAGCCCAGCAAGAGTACCTAGAAGCCGTGACCCAGGG
CCATGGCGCTTACCTGATGAGTCAGGATGCTCCGGACGTTTTACTGTAAGTGTTGG
AAACTTACCCCCTAAGGCTAAGGTTCTTATAAAAATTACCTACATCACAGAACTCAG
CATCCTGGGCACTGTTGGTGTCTTTTTCATGCCCGCCACCGTAGCACCCTGGCAACA
GGACAAGGCTTTGAATGAAAACCTTCAGGATACAGTAGAGAAGATTTGTATAAAAG
AAATAGGAACAAAGCAAAGCTTCTCTTTGACTATGTCTATTGAGATGCCGTATGTGA
TTGAATTCATTTTCAGTGATACACATGAACTGAAACAAAAGCGCACAGACTGCAAA
GCTGTCATTAGCACCATGGAAGGCAGCTCCTTAGACAGCAGTGGATTTTCTCTCCAC
ATCGGTTTGTCTGCTGCCTATCTCCCAAGAATGTGGGTTGAAAAACATCCAGAAAAA
GAAAGCGAGGCTTGCATGCTTGTCTTTCAACCCGATCTCGATGTCGACCTCCCTGAC
CTAGCCAGTGAGAGCGAAGTGATTATTTGTCTTGACTGCTCCAGTTCCATGGAGGGT
GTGACATTCTTGCAAGCCAAGCAAATCGCCTTGCATGCGCTGTCCTTGGTGGGTGAG
AAGCAGAAAGTAAATATTATCCAGTTCGGCACAGGTTACAAGGAGCTATTTTCGTAT
CCTAAGCATATCACAAGCAATACCATGGCAGCAGAGTTCATCATGTCTGCCACACCT
ACCATGGGAACACAGACTTCTGGAAAACACTCCGATATCTTAGCTTATTGTACCCT
GCTCGAGGGTCACGGAACATCCTCCTGGTGTCTGATGGGCACCTCCAGGATGAGAGC
CTGACATTACAGCTCGTGAAGAGGAGCCGCCCGCACACCAGGTTATTCGCCTGCGGT
ATCGGTTCTACAGCAAATCGTCACGTCTTAAGGATTTTGTCCCAGTGTGGTGCCGGA
GTATTTGAATATTTTAATGCAAAATCCAAGCATAGTTGGAGAAAACAGATAGAAGA
CCAAATGACCAGGCTATGTTCTCCGAGTTGCCACTCTGTCTCCGTCAAATGGCAGCA
ACTCAATCCAGATGTGCCCGAGGCCCTGCAGGCCCCAGCCCAGGTGCCGTCCTTGTT
TCTCAATGATCGACTCCTTGTCTATGGATTCATTCCTCACTGCACACAGGCAACTCTG
TGTGCACTAATTCAAGAGAAAGAATTTCGTACAATGGTGTCGACTACTGAGCTTCAG
AAGACAACTGGAACTATGATCCACAAGCTGGCAGCCCGAGCTCTAATCAGAGATTA
TGAAGATGGCATTCTTCACGAAAATGAAACCAGTCATGAGATGAAAAAACAAACCT
TGAAATCTCTGATTATTAAACTCAGTAAAGAAAACTCTCTCATAACACAATTTACAA
GCTTTGTGGCAGTTGAGAAAAGGGATGAGAATGAGTCGCCTTTTCCTGATATTCCAA
AAGTTTCTGAACTTATTGCCAAAGAAGATGTAGACTTCCTGCCCTACATGAGCTGGC
AGGGGGGAGCCCCAAGAAGCCGTCAGGAACCAGTCTCTTTTAGCATCCTCTGAGTGGC
CAGAATTACGTTTATCCAAACGAAACATAGGGAAAATTCCATTTTCCAAAAGAAAA
ATGGAATTATCTCAGCCAGAAGTTTCTGAAGATTTTGAAGAGGATGGCTTAGGTGTA
CTACCAGCTTTCACATCAAATTTGGAACGTGGAGGTGTGGAAAAGCTATTGGATTTA
AGTTGGACAGAGTCATGTAAACCAACAGCAACTGAACCACTATTTAAGAAAGTCAG
TCCATGGGAAACATCTACTTCTAGCTTTTTTCCTATTTTGGCTCCGGCCGTTGGTTCCT
ATCTTCCCCCGACTGCCCGCGCTCACAGTCCTGCTTCCTTGTCTTTTGCCTCATATCGT
CAGGTAGCTAGTTTCGGTTCAGCTGCTCCTCCCAGACAGTTTGATGCATCTCAATTCA
GCCAAGGCCCTGTGCCTGGCACTTGTGCTGACTGGATCCCACAGTCGGCGTCTTGTC
CCACAGGACCTCCCCAGAACCCACCTTCTTCACCCTATTGTGGCATTGTTTTTCAGG
GAGCTCATTAAGCTCTGCACAGTCTGCTCCACTGCAACATCCTGGAGGCTTTACTAC
CAGGCCTTCTGCTGGCACCTTCCCTGAGCTGGATTCTCCCCAGCTTCATTTCTCTCTT
CCTACAGACCCTGATCCCATCAGAGGTTTTGGGTCTTATCATCCCTCTGCTTCCTCTC
CTTTTTCATTTTCAACCTTCCGCAGCCTCTTTGACTGCCAACCTTAGGCTGCCAATGGC
CTCTGCTTTACCTGAGGCTCTTTGCAGTCAGTCCCGGACTACCCCAGTAGATCTCTGT
CTTCTAGAAGAATCAGTAGGCAGTCTCGAAGGAAGTCGATGTCCTGTCTTTGCTTTTC
AAAGTTCTGACACAGAAAGTGATGAGCTATCAGAAGTACTTCAAGACAGCTGCTTTT
TACAAATAAAAATGTGATACAAAGATGACAGTATCCTGTGCTTTCTGGAAGTAAAAG
AAGAGGATGAAATAGTGTGCATACAACACTGGCAGGATGCTGTGCCTTGGACAGAA
CTCCTCAGTCTACAGACAGAGGATGGCTTCTGGAAACTTACACCAGAACTGGGACTT
ATATTAAATCTTAATACAAATGGTTTGCACAGCTTTCTTAAACAAAAAGGCATTCAA
TCTCTAGGTGTAAAAGGAAGAGAATGTCTCCTGGACCTAATTGCCACAATGCTGGTA
CTACAGTTTATTCGCACCAGGTTGGAAAAGAGGGAATAGTGTTCAAATCACTGATG
AAAATGGATGACGCTTCTATTTCCAGGAATATTCCCTGGGCTTTTGAGGCAATAAAG
CAAGCAAGTGAATGGGTAAGAAGAACTGAAGGACAGTACCCATCTATCTGCCCACG |

TABLE 1-continued

Exemplary human PARP4 Nucleic acid and Amino acid Sequences

| SEQ ID NO | Sequence |
|---|---|
|  | GCTTGAACTGGGGAACGACTGGGACTCTGCCACCAAGCAGTTGCTGGGACTCCAGC<br>CCATAAGCACTGTGTCCCCTCTTCATAGAGTCCTCCATTACAGTCAAGGCTAA |
| 2 | MVMGIFANCIFCLKVKYLPQQQKKKLQTDIKENGGKFSFSLNPQCTHIILDNADVLSQYQ<br>LNSIQKNHVHIANPDFIWKSIREKRLLDVKNYDPYKPLDITPPPDQKASSSEVKTEGLCPD<br>SATEEEDTVELTEFGMQNVEIPHLPQDFEVAKYNTLEKVGMEGGQEAVVVELQCSRDS<br>RDCPFLISSHFLLDDGMETRRQFAIKKTSEDASEYFENYIEELKKQGFLLREHFTPEATQL<br>ASEQLQALLLEEVMNSSTLSQEVSDLVEMIWAEALGHLEHMLLKPVNRISLNDVSKAEG<br>ILLLVKAALKNGETAEQLQKMMTEFYRLIPHKGTMPKEVNLGLLAKKADLCQLIRDMV<br>NVCETNLSKPNPPSLAKYRALRCKIEHVEQNTEEFLRVRKEVLQNHHSKSPVDVLQIFRV<br>GRVNETTEFLSKLGNVRPLLHGSPVQNIVGILCRGLLLPKVVEDRGVQRTDVGNLGSGIY<br>FSDSLSTSIKYSHPGETDGTRLLLICDVALGKCMDLHEKDFSLTEAPPGYDSVHGVSQTA<br>SVTTDFEDDEFVVYKTNQVKMKYIIKFSMPGDQIKDFHPSDHTELEEYRPEFSNFSKVED<br>YQLPDAKTSSSTKAGLQDASGNLVPLEDVHIKGRIIDTVAQVIVFQTYTNKSHVPIEAKYI<br>FPLDDKAAVCGFEAFINGKHIVGEIKEKEEAQQEYLEAVTQGHGAYLMSQDAPDVFTVS<br>VGNLPPKAKVLIKITYITELSILGTVGVFFMPATVAPWQQDKALNENLQDTVEKICIKEIG<br>TKQSFSLTMSIEMPYVIEFIFSDTHELKQKRTDCKAVISTMEGSSLDSSGFSLHIGLSAAYL<br>PRMWVEKHPEKESEACMLVFQPDLDVDLPDLASESEVIICLDCSSSMEGVTFLQAKQIAL<br>HALSLVGEKQKVNIIQFGTGYKELFSYPKHITSNTMAAEFIMSATPTMGNTDFWKTLRY<br>LSLLYPARGSRNILLVSDGHLQDESLTLQLVKRSRPHTRLFACGIGSTANRHVLRILSQCG<br>AGVFEYFNAKSKHSWRKQIEDQMTRLCSPSCHSVSVKWQQLNPDVPEALQAPAQVPSL<br>FLNDRLLVYGFIPHCTQATLCALIQEKEFRTMVSTTELQKTTGTMIHKLAARALIRDYED<br>GILHENETSHEMKKQTLKSLIIKLSKENSLITQFTSFVAVEKRDENESPFPDIPKVSELIAKE<br>DVDFLPYMSWQGEPQEAVRNQSLLASSEWPELRLSKRKHRKIPFSKRKMELSQPEVSED<br>FEEDGLGVLPAFTSNLERGGVEKLLDLSWTESCKPTATEPLFKKVSPWETSTSSFFPILAP<br>AVGSYLPPTARAHSPASLSFASYRQVASFGSAAPPRQFDASQFSQGPVPGTCADWIPQSA<br>SCPTGPPQNPPSSPYCGIVFSGSSLSSAQSAPLQHPGGFTTRPSAGTFPELDSPQLHFSLPTD<br>PDPIRGFGSYHPSASSPFHFQPSAASLTANLRLPMASALPEALCSQSRTTPVDLCLLEESV<br>GSLEGSRCPVFAFQSSDTESDELSEVLQDSCFLQIKCDTKDDSILCFLEVKEEDEIVCIQH<br>WQDAVPWTELLSLQTEDGFWKLTPELGLILNLNTNGLHSFLKQKGIQSLGVKGRECLLD<br>LIATMLVLQFIRTRLEKEGIVFKSLMKMDDASISRNIPWAFEAIKQASEWVRRTEGQYPSI<br>CPRLELGNDWDSATKQLLGLQPISTVSPLHRVLHYSQG |

SEQ ID NO. 1: Nucleotide sequence for human PARP4 mRNA (NCBI GenBank NM_006437.3)
SEQ ID NO. 2: Amino acid sequence for human PARP4 (NCBI GenBank NP_006428.2)

EXAMPLES

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

Example 1. Immobilization of Molecules by ADP-Ribosylation

Figure 5A:
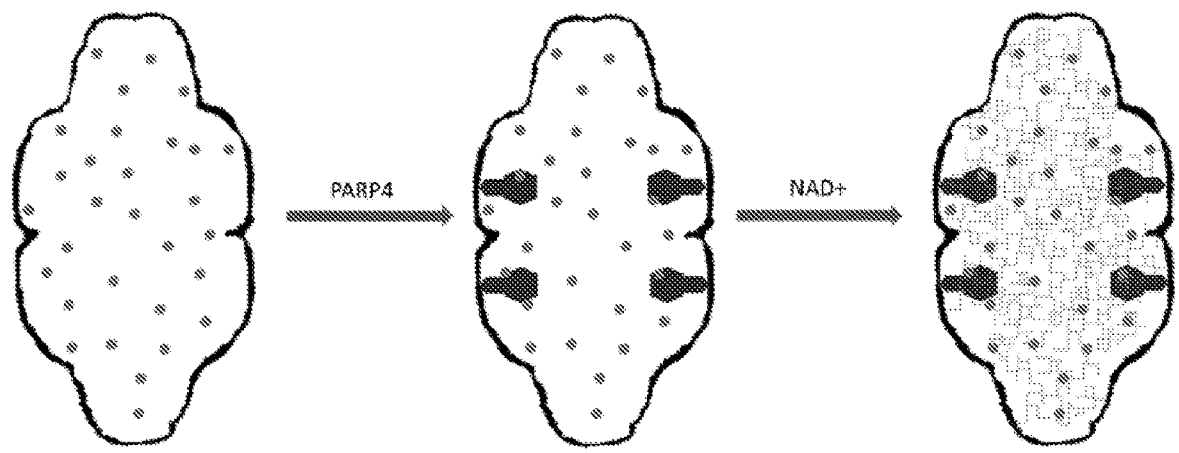
FIG. 5A-FIG. 5C show a schematic of different methods for PARP4 catalyzed ADP-ribosylation within the vault cavity.
Figure 5B:
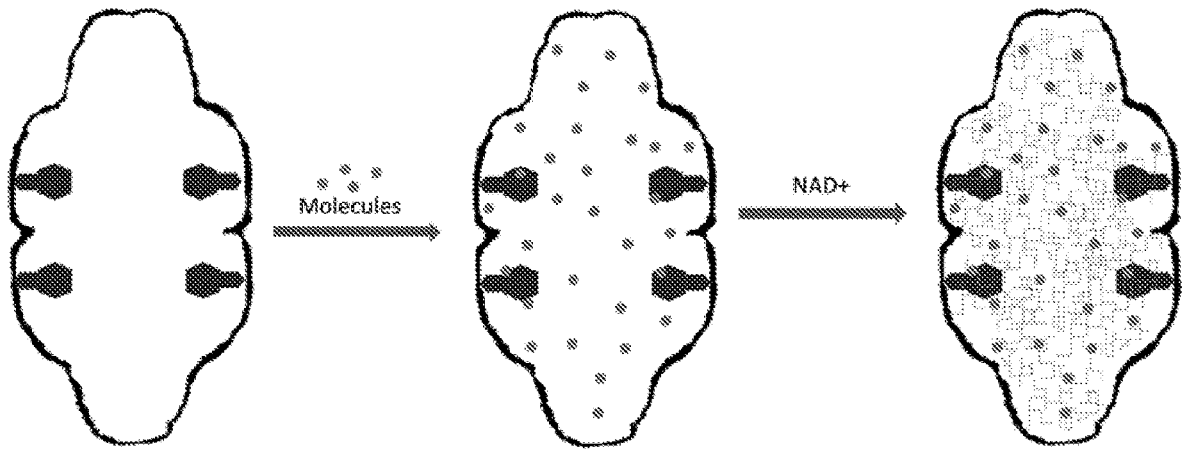
Figure 5C:
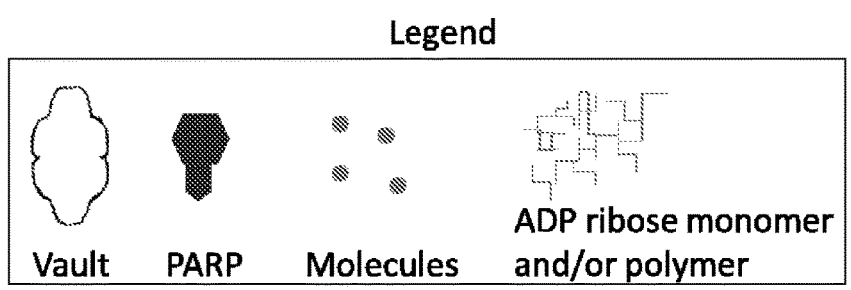

To achieve ADP-ribosylation of vault enclosed passenger molecules, vaults are synthesized using either an in vitro cell-free protein expression system or a cell-based protein expression system. Vaults are passively loaded with large passenger molecules (see FIG. 5A) during synthesis. Alternatively, or additionally, small passenger molecules that can readily diffuse into the vault are loaded after synthesis (see FIG. 5B). ADP-ribosylation is carried out by adding a PARP4 or engineered PARP4 variant during vault synthesis or to the completed vault and incubating the vault in the presence of the substrate, NAD+, and an acceptor molecule. Vaults produced in cell-based systems contain a profile of cytoplasmic molecules from the producing cell which may be of interest in certain applications, and additionally may accommodate small passenger molecules after vault synthesis is complete. To initiate ADP-ribosylation, PARP4 or engineered PARP4 variants are added to vaults before or after purification and then incubated in the presence of NAD+.

The passenger molecule of interest naturally contains an acceptor site for ADP-ribosylation. Alternatively, the passenger molecule does not contain an acceptor site, and an inert molecule, or excipient, is added in addition to the molecule of interest. Alternatively, a vault protein contains the acceptor site.

Example 2. Altering the Physicomechanical Properties of Vault Particles

Figure 6A:
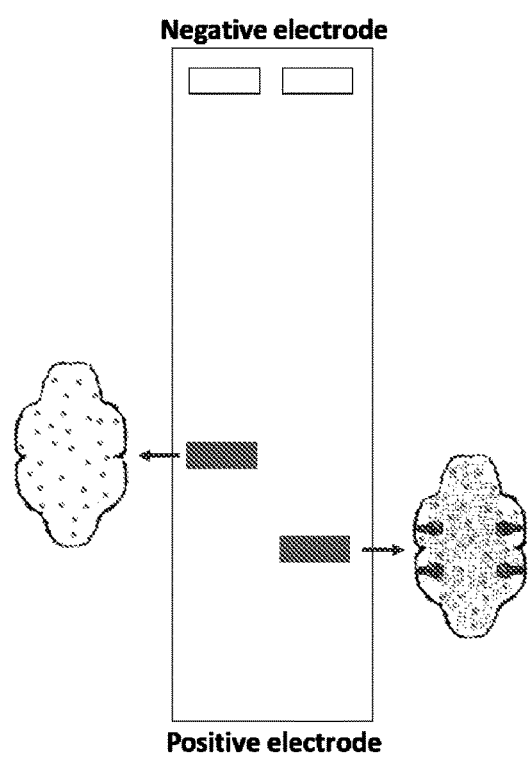
FIG. 6A-FIG. 6B show electrophoretic migration of vaults in a native agarose gel.
Figure 6B:
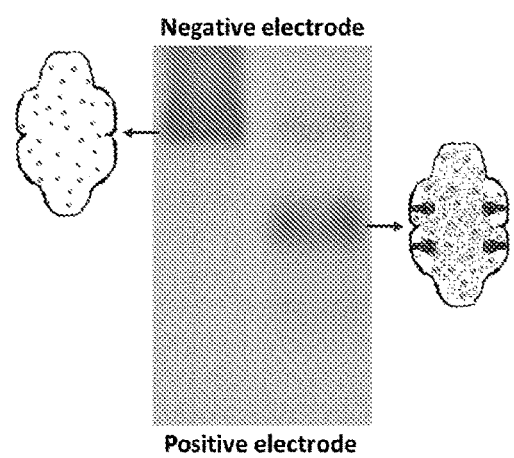

ADP-ribosylation was carried out based on previously described methods (Kickhoefer, Siva, et al., 1999; Tulin, 2011). 14 μg of purified vaults with or without human PARP4, synthesized in a cell-free or a cell-based protein expression system, was added to 15 μl of ADP-ribosylation reaction buffer (50 mM Tris-HCl, pH 8.0, 4 mM MgCl$_2$, 0.4 mM dithiothreitol (DTT) and 1 μl of tartrazine (a small molecule (533 daltons) from TCI Chemicals, at 40 mg/ml in water). The reaction was initiated by the addition of 1 μl of the substrate NAD+ (MilliporeSigma, at 75.36 mM in water) and was incubated at room temperature for 15-60 minutes. Changes in the physicomechanical properties was measured by native agarose gel electrophoresis. The completed reaction was mixed with 6X glycerol bromophenol blue loading dye, applied to respective wells of a 0.7% agarose-Tris-boric acid-EDTA (TBE) gel and a voltage was applied. Electrophoretic mobility was visualized by Coomassie blue staining and LI-COR imaging. Vaults containing PARP4 and incubated with tartrazine and NAD+ migrated faster through the agarose gel than vaults without PARP4. As agarose gel electrophoresis separates molecules based on charge (see FIG. 6B), vaults containing an ADP-ribose matrix are more negatively charged and thus migrate faster.

Quantitative measurement of electrostatic charge is measured as the zeta potential, using the qNANO GOLD (Izon Science, Christchurch, New Zealand).

Vault encapsulated tartrazine is quantified by extracting the vault band from the agarose, measuring the absorbance at 427 nm, for tartrazine, and 280 nm, for protein. The concentration of tartrazine is determined using a tartrazine standard curve, and is compared between reactions with and without PARP4 and reactions with and without NAD+.

Figure 7A:
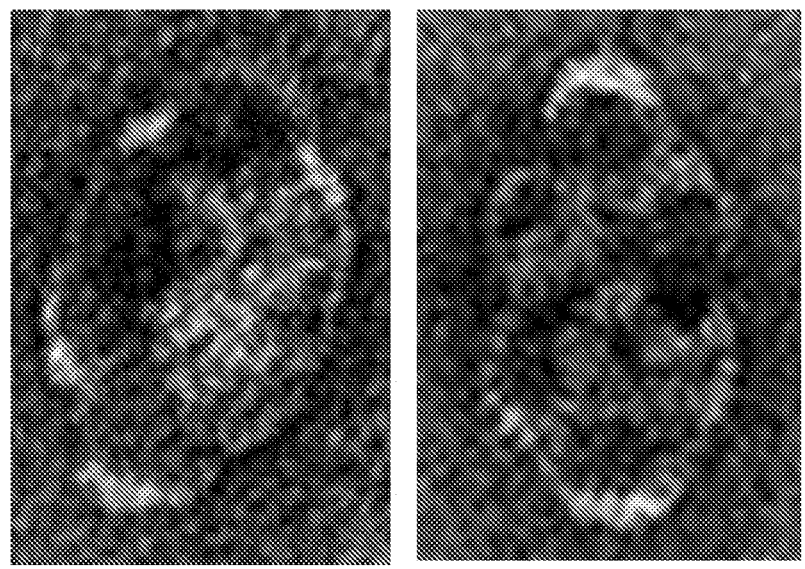
FIG. 7A shows electron micrographs of uranyl acetate stained vaults that contain passenger molecules.
Figure 7B:
FIG. 7B shows electron micrographs of uranyl acetate stained vaults that are empty.

Example 3. Assessing the Physicomechanical Properties of Altered Vault Particles To assess compressive strength conferred by an ADP-ribose matrix (e.g., as described in Example 1) within the vault particle, uranyl acetate staining and electron microscopy is used. ADP-ribosylation within the vault particle is carried with 10-15 μg of vaults, with and without PARP4, 1 μl of tartrazine (TCI Chemicals, 40 mg/ml in water), 1 μl of the substrate NAD+ (MilliporeSigma, 3.75 mM) in 15 μl ADP-ribosylation reaction buffer (50 mM Tris-HCl, pH 8.0, 4 mM $MgCl_2$, 0.4 mM dithiothreitol (DTT). The reaction is incubated for 30 minutes at room temperature. Vaults are purified by agarose gel electrophoresis and gel extraction. Purified vaults are adsorbed onto carbon-coated holey film grids for 1 min at 4° C., stained with 1% uranyl acetate for 5 min at 4° C., and the resulting grids will be dried on filter paper. Uranyl acetate stained samples are evaluated by electron microscopy. Vault particles with greater density and compressive strength display an ovoid shape with smoother sides (FIG. 7A), whereas empty vaults or vaults without an ADP-ribose matrix are flatter and have pronounced invaginations at the waist (FIG. 7B).

Example 4. Assessing Vault Association with Target Cell Nuclei

Vaults disclosed herein may advantageously associate with a nucleus of a target cell. To demonstrate this, the fluorescent molecule Cy3 carboxylic acid, trisulfo is incubated with vaults that contain PARP4 in the presence of NAD+. After incubation, immobilization of Cy3 carboxylic acid, trisulfo is characterized by electrophoretic mobility in agarose gel and typhoon imaging. The vault band is excised and eluted from the gel. Gel purified vaults is incubated with the human monocytic THP-1 cells grown on a glass slide or with the human epithelial 293T cells, human breast epithelial MCF7 cells, or human osteosarcoma U2OS cells. After 30 minutes, and 1, 2 and 6 hours, cells are washed, stained and fixed with paraformaldehyde. Confocal microscopy is used to determine the subcellular localization of the Cy3 carboxylic acid, trisulfo molecules. Relative intensity of Cy3 in subcellular compartments, particularly the nucleus, is compared between treatments.

Example 5. Comparing Efficacy of Free Therapeutic Agent to Vault-Delivered Therapeutic Agent Doxorubicin is immobilized within a vault particle described herein and agarose gel purified as described. Vaults containing immobilized doxorubicin or free doxorubicin is applied to MCF7 breast cancer cells and incubated for 2, 6 and 24 hours. After 2 and 6 hours, cells are prepared for confocal microscopy. The cells are washed 3× with phosphate buffered saline (PBS) to remove free doxorubicin or doxorubicin immobilized vaults, fixed with 2% paraformaldehyde for 15 min at room temperature, washed 2× with PBS and incubated with the nuclear stain Hoechst 33342 (5 ng/ml in PBS) for 10 min at room temperature. The subcellular location of doxorubicin is visualized by doxorubicin autofluorescence with 488 nm excitation and Hoechst 33342 emission with 350 nm excitation. Doxorubicin delivered by vaults will enter the nucleus more rapidly and reach a higher nuclear concentration compared to free doxorubicin as the vault will shield the doxorubicin molecules from cellular drug efflux pumps. After 24 hours, the MTT assay is used to measure cell viability; ADP-ribose matrix immobilized doxorubicin within the vault particle will be compared to free doxorubicin. Doxorubicin delivered by vaults will be more effective than free doxorubicin.

Example 6. Packaging of DNA, RNA or Protein Molecules by Electrostatic Interactions Charged, hydrophobic and/or polar molecules accessible in the inner vault cavity in the rat MVP crystal structure (PBD ID: 4V60) and other MVP structures are identified using coordinates public databases (e.g., RCSB PDB, www.resb.org) and molecular visualization software (e.g., Pymol, www.pymol.org). Based on the properties of the passenger molecule, amino acids within Regions I-III (FIG. 10A) are mutated, or additional amino acids are inserted, to yield a local change in electrostatic, hydrophobic or polar properties. To reduce improper folding of the MVP chain/vault particle, insertions primarily occur within internal loops.

Passenger molecules are added to the vault assembly reaction or after vault assembly as described herein. Passenger molecules include plasmid DNA (e.g., CRISPR plasmids), RNA (e.g., non-coding RNA, mRNA), proteins and peptides. Packaging and release of passenger molecules is measured with standard methods.

Example 7. Delivery of Vault Particles Engineered to Express a Peptide Ligand in the Shoulder Domain In many types of cancer, including breast, ovarian and prostate cancer, gastrin-releasing peptide receptor (GRP-R) is overexpressed which makes GRP-R a suitable target for both therapy and imaging. An 8-amino acid peptide of the ligand GRP having the sequence Gin-Trp-Ala-Val-Gly-His-Leu-Met (SEQ ID NO.: 3)-NH2 has been found to have affinity for the GRP-R (Accardo et al., EJNMMI Research 2016 Dec. 6 (1): 17). To target vaults to GPR-R overexpressing cells, the 8-amino acid peptide was cloned into the unstructured shoulder region following Gly613 to extend the region by eight amino acids by In-Fusion® PCR Cloning System (Takara Bio USA, Mountain View, CA). The expression vector, pEU E01-MCS (Cell Free Sciences, Yokohama, Japan) containing the rat major vault protein (MVP) sequence engineered with an AfeI restriction site (AGCGCT) in the shoulder region between Gly613 and Pro614 was digested with AfeI (FIG. 11B). Complementary 57-mer oligonucleotides coding for the 8-amino acid peptide flanked by homologous sequences for In-Fusion® cloning into the open vector were hybridized to create the insert (forward oligonucleotide, (SEQ ID NO.: 4)
CTGAAGACACAGGTAGCGATTACAAAGATGACGATGATAAGGCTCCTGAT
GGCACAC,
and reverse oligonucleotide, (SEQ ID NO.: 5)
GTGTGCCATCAGGAGCCTTATCATCGTCATCTTTGTAATCGCTACCTGTG
TCTTCAG).

Insertion was confirmed by sequence analysis.

Vault particles were produced by an in vitro cell-free translation using WEPRO® 7240 wheat germ extract and SUBAMIX® translation buffer (Cell Free Sciences, Yokohama, Japan). Assembly of GRP-Vaults was confirmed by immunogold electron microscopy. Wild type (WT) or GRP-Vaults were adsorbed to a formvar coated Nickel grid, stabilized with carbon. Grids were washed twice and blocked with blocking buffer (50 mM Tris-HCL, pH 8.0-100 mM NaCl-1% BSA). Grids were applied to rabbit anti-GRP, Cat #ab22623, (Abcam, Cambridge, MA), diluted 1:20 in blocking buffer and incubated for 1 hour at room temperature, then washed twice. The grids were applied to goat anti-rabbit IgG H&L-10 nm gold, Cat #ab27234, (Abcam, Cambridge, MA), diluted 1:20 in blocking buffer and incubated for 1 hour at room temperature, then washed twice. The grids were stained with 1% uranyl acetate then visualized by transmission electron microscopy using a JEM1200EX electron microscope (JEOL, Tokyo, Japan) (FIG. 12A).

Specific targeting (e.g., to ORP-R overexpressing cells) was measured by performing in vitro binding experiments with GRP-R expressing PC-3 human prostate cancer cells (FIG. 12B) and GRP-R negative cell line (negative control). Cells were plated in an 8-well chamber slide (Nalge Nunc, Rochester, New York) and incubated overnight. Both cell lines are treated with DyLight®-488 (ThermoFisher Scientific, Waltham, MA) labeled vault particles, one set with bombesin peptide and another set without the bombesin peptide (negative control). Incubation was carried out at 4° C.' for 1 hour. Cells were washed three times with 1% FBS-PBS and fixed with paraformaldehyde for 5 min. EMS Immuno Mount DAPI and DABCO, Cat #17989-97 (Electron Microscopy Sciences, Hatfield, PA) was applied to the slide and a coverslip was added. Images were acquired with an epifluorescence microscope at 1000× magnification (FIG. 12B).

Example 8. Vault Particles Engineered to Express an Epitope Tag in the Shoulder Domain Epitope tags are ligands commonly used to label proteins for which a well-established repertoire of antibodies and other reagents have been developed to detect them. The hydrophilic 8 amino acid peptide, DYKDDDDK (SEQ ID NO.: 6), was inserted into the unstructured should domain using strategy 1 outlined in FIG. 11B. Complementary 57-mer oligonucleotides coding for the 8-amino acid peptide flanked by homologous sequences were hybridized to create the insert (forward oligonucleotide, (SEQ ID NO.: 7)
CTGAAGACACAGGTAGCGAGTGGGCGGTGGGGCACTTAATGGCTCCTGAT
GGCACAC,
and reverse oligonucleotide, (SEQ ID NO.: 8)
GTGTGCCATCAGGAGCCATTAAGTGCCCCACCGCCCACTCGCTACCTGTG
TCTTCAG), and cloned into the AfeI digested rat MVP-pEU-E01-MCS vector by In-Fusion® cloning. Insertion was confirmed by sequence analysis. DYKDDDDK (SEQ ID NO.: 6) tagged vault particles were produced by an in vitro cell-free translation using WEPRO® 7240 wheat germ extract and SUBAMIX® translation buffer (Cell Free Sciences, Yokohama, Japan). DYKDDDDK (SEQ ID NO.: 6)-vault particle assembly was confirmed by native agarose gel electrophoresis and Coomassie Blue staining.

---

What is claimed is:

1. An engineered vault particle comprising multiple copies of a major vault protein (MVP) which are engineered to comprise a mutation of at least one amino acid of a shoulder domain of a wild-type MVP and wherein the mutated shoulder domain comprises a peptide of interest on the outer-facing surface of the engineered vault particle, wherein the mutated shoulder domain comprises a region spanning from methionine at position 608 to proline at position 620 of SEQ ID NO. 9 or wherein the mutated shoulder domain comprises a region spanning from threonine at position 608 to proline at position 620 of SEQ ID NO. 10, wherein the mutation of at least one amino acid results in an even distribution of the mutation around the shoulder domain or circumference of the shoulder domain of the engineered vault particle, and wherein the mutation of at least one amino acid is an insertion of the peptide of interest which is an epitope tag having the sequence DYKDDDDK (SEQ ID) NO: 6) or a gastrin-releasing peptide receptor (GRP-R)-binding peptide having the sequence QWAVGHLM (SEQ ID NO.: 3).

* * * * *